United States Patent
Denolly

(10) Patent No.: US 6,893,423 B2
(45) Date of Patent: May 17, 2005

(54) INJECTION SYRINGE WITH MOBILE NEEDLE GUARD

(75) Inventor: Pascal Denolly, Jardin (FR)

(73) Assignee: Sedat, Irigny (FR)

( * ) Notice: Subject to any disclaimer, the term of this patent is extended or adjusted under 35 U.S.C. 154(b) by 256 days.

(21) Appl. No.: 10/169,159

(22) PCT Filed: Oct. 22, 2001

(86) PCT No.: PCT/FR01/03277
§ 371 (c)(1),
(2), (4) Date: Jun. 28, 2002

(87) PCT Pub. No.: WO02/36186
PCT Pub. Date: May 10, 2002

(65) Prior Publication Data
US 2002/0193747 A1 Dec. 19, 2002

(30) Foreign Application Priority Data
Nov. 3, 2000 (FR) .............................. 00 14138

(51) Int. Cl.[7] .............................................. A61M 5/32
(52) U.S. Cl. ........................ 604/192; 604/201; 604/110
(58) Field of Search ................................ 604/110, 187, 604/197, 198, 263, 218, 19, 93.01, 192–196, 200, 201, 203, 216, 244, 181

(56) References Cited

U.S. PATENT DOCUMENTS

| | | | |
|---|---|---|---|
| 4,887,998 A | | 12/1989 | Martin et al. |
| 5,720,727 A | * | 2/1998 | Alexander et al. .......... 604/110 |
| 5,882,342 A | | 3/1999 | Cooper |
| 5,891,092 A | * | 4/1999 | Castellano ................... 604/110 |
| 6,565,540 B1 | * | 5/2003 | Perouse et al. ............. 604/192 |
| 6,569,124 B1 | * | 5/2003 | Perouse ....................... 604/198 |
| 6,679,864 B2 | * | 1/2004 | Gagnieux et al. ........... 604/198 |

FOREIGN PATENT DOCUMENTS

| | | |
|---|---|---|
| FR | 2757066 A1 | 6/1998 |
| WO | WO 93/00949 | 1/1993 |
| WO | WO 00/56383 | 9/2000 |

* cited by examiner

Primary Examiner—Nicholas D. Lucchesi
Assistant Examiner—Jennifer J Maynard
(74) Attorney, Agent, or Firm—Sughrue Mion, PLLC

(57) ABSTRACT

The injection syringe has at least one syringe body (12) provided with a needle (22) and a pusher (14) mounted so as to be able to move in the body (12). The syringe has a movable guard (36) for protecting the injection end (22A) of the needle. The guard (36) is able to move with respect to the body (12) between a position retracted in the body (12) and an active protection position. The guard (36) and the body (12) have associated projecting and recessed reliefs for holding the guard in a retracted position. It has a retractable member (70) for positive holding of the engagement of the said associated reliefs, when the guard (36) is in a retracted position. The pusher (14) and the said holding member (70) are adapted for a retraction of the said holding member (70) under the action of the pushing in of the pusher (14) into the body, at the end of injection, providing a release of the positive holding of the engagement of the associated reliefs.

19 Claims, 20 Drawing Sheets

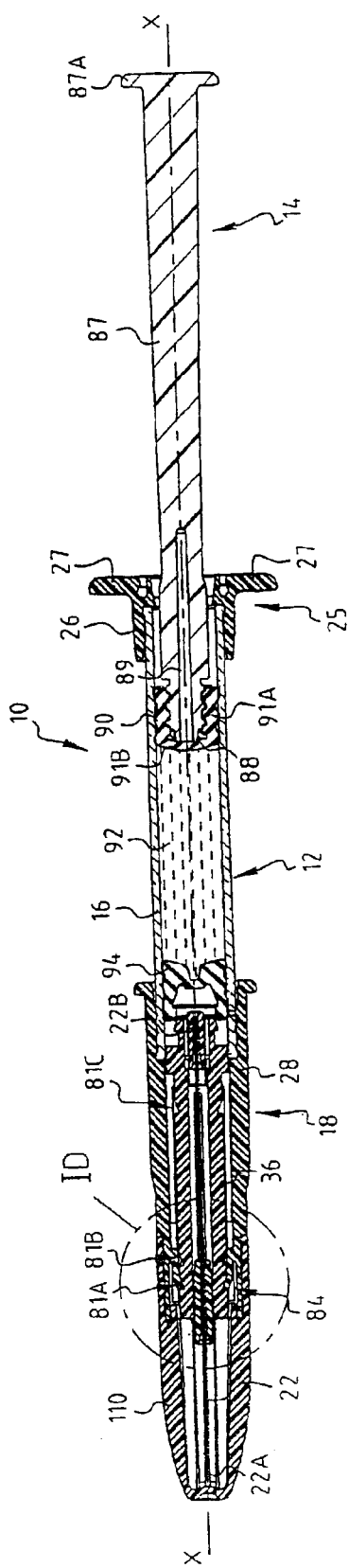
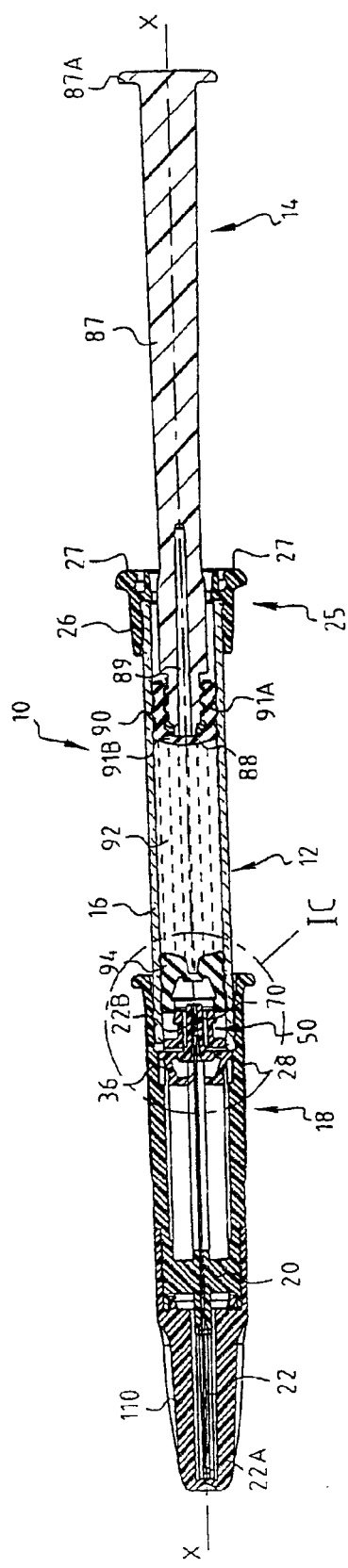
FIG.1A
FIG.1B

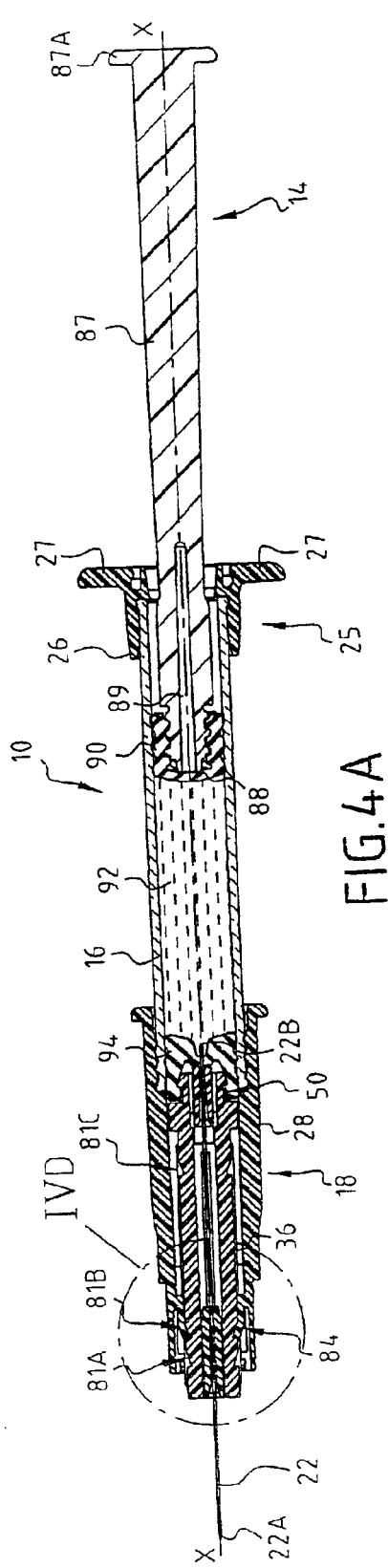
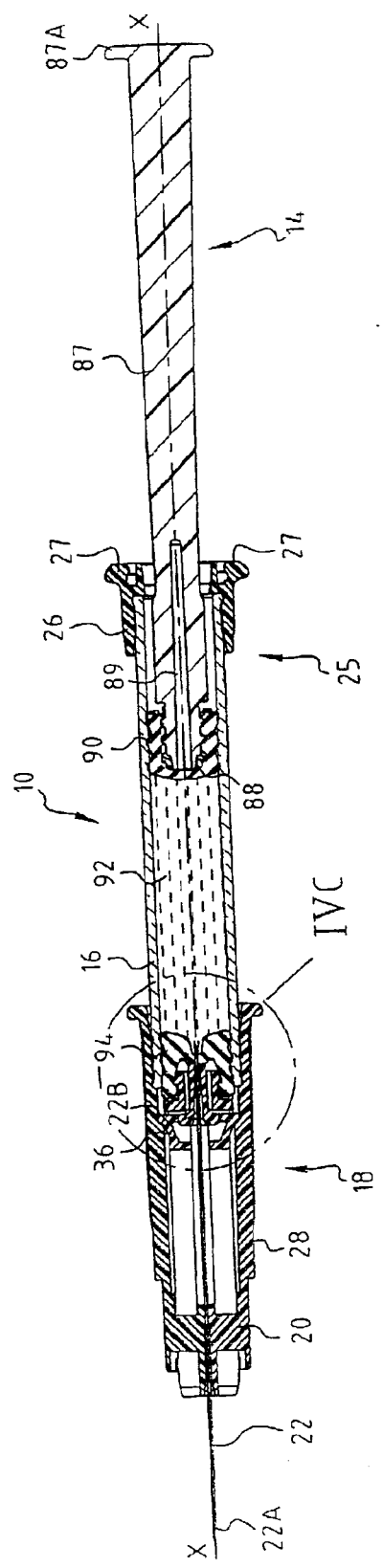

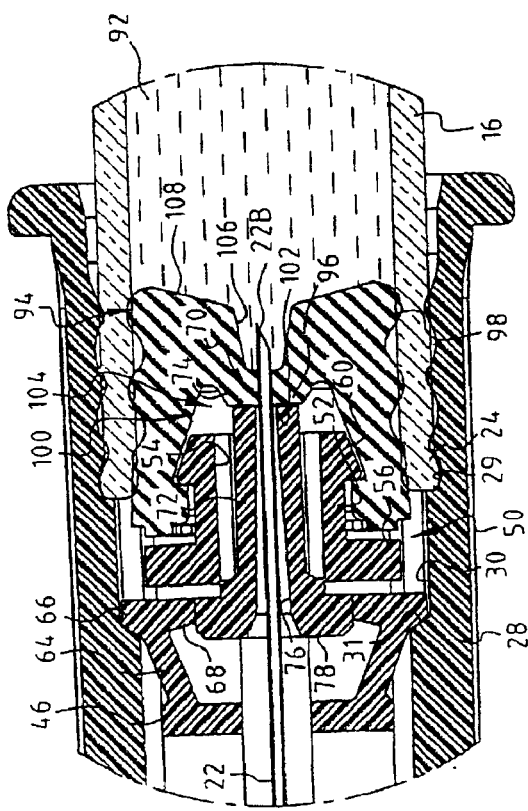

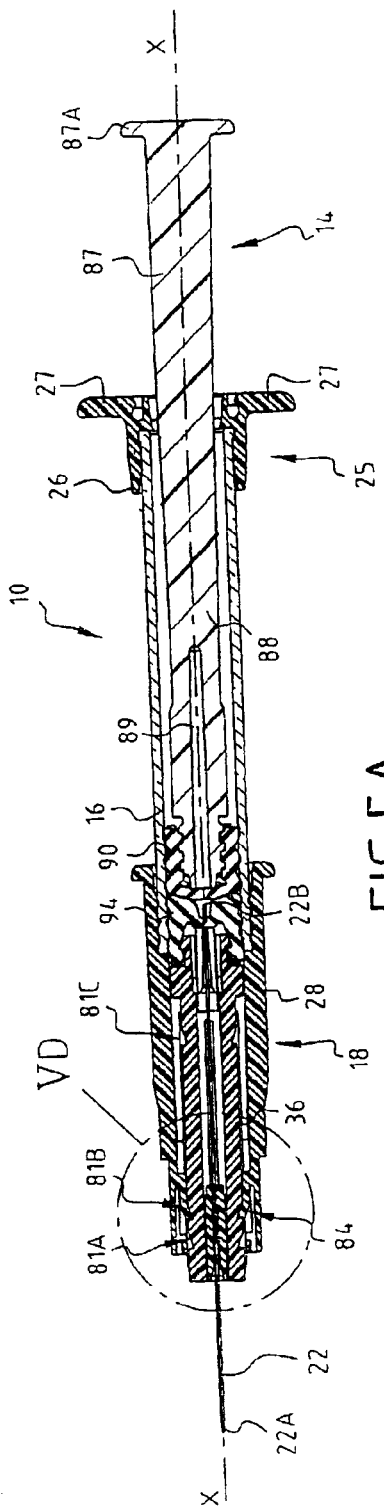
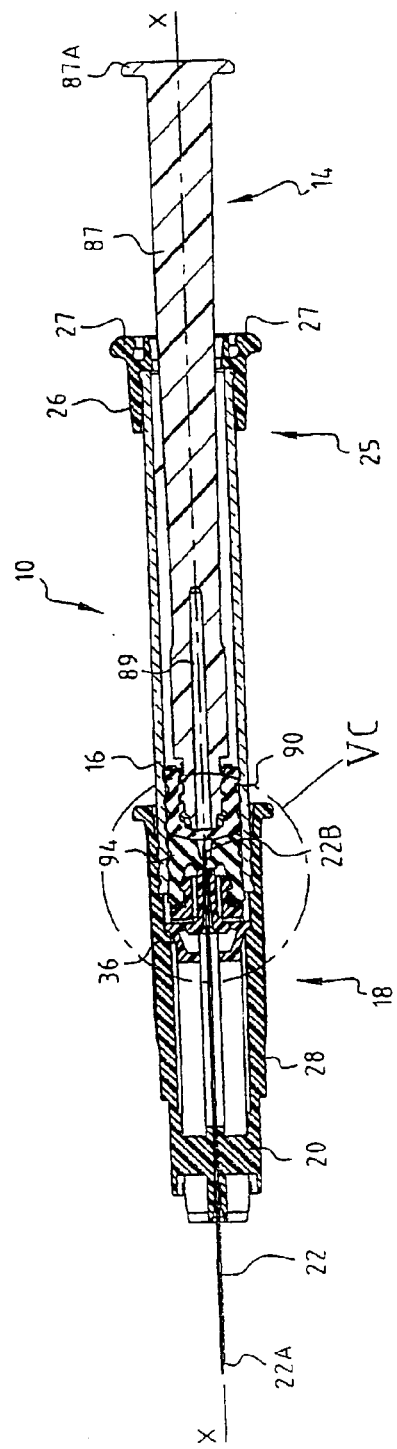
FIG.5A
FIG.5B

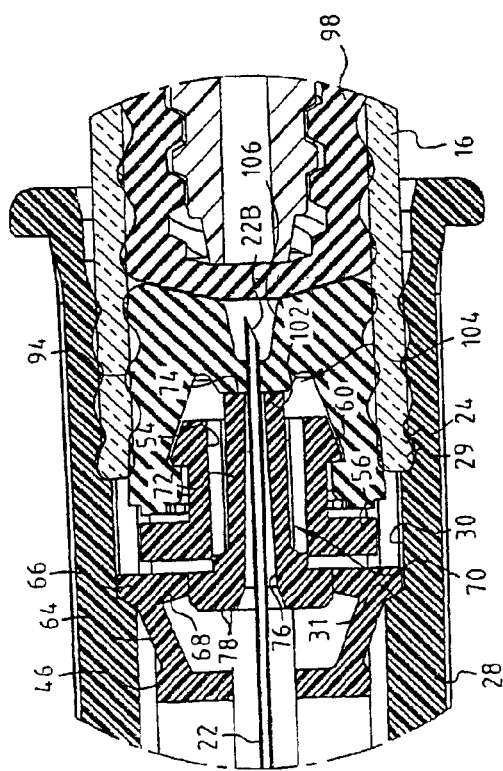

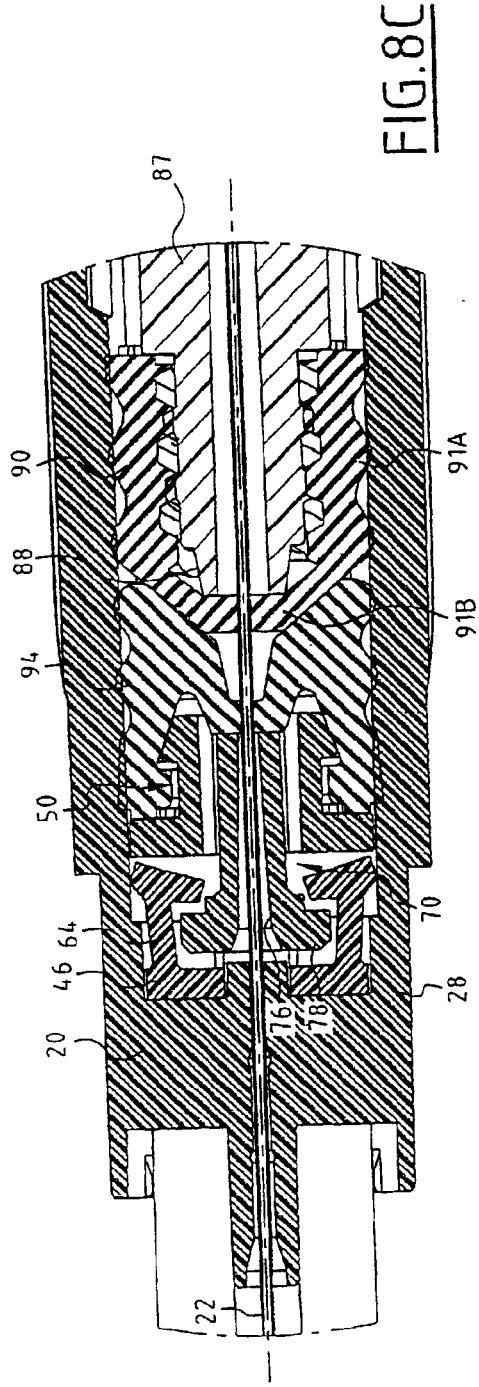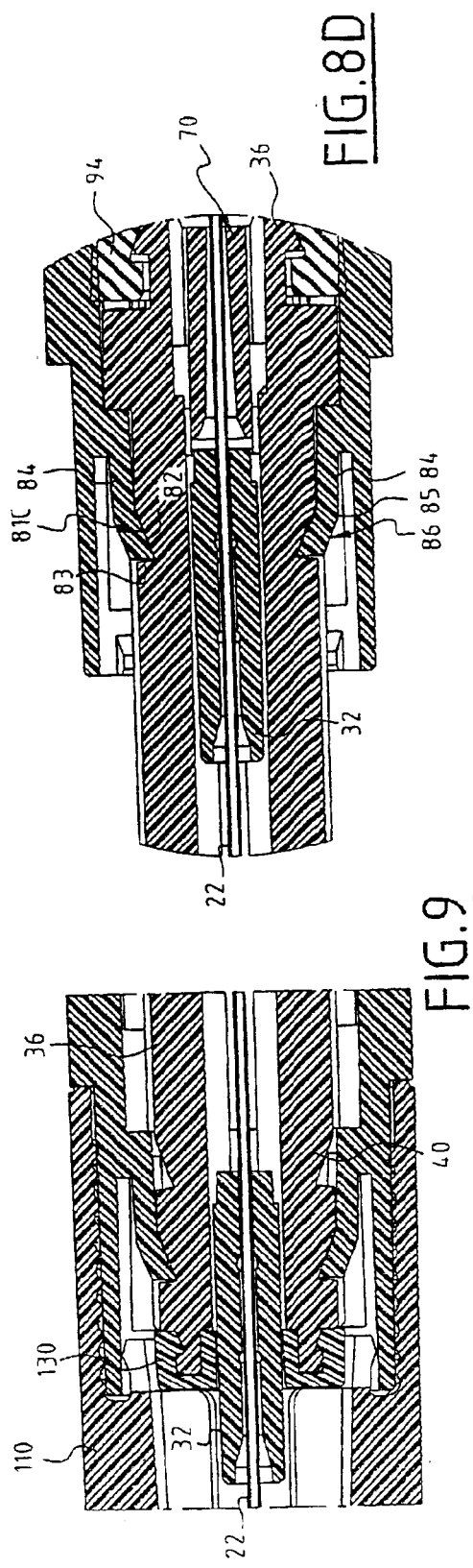

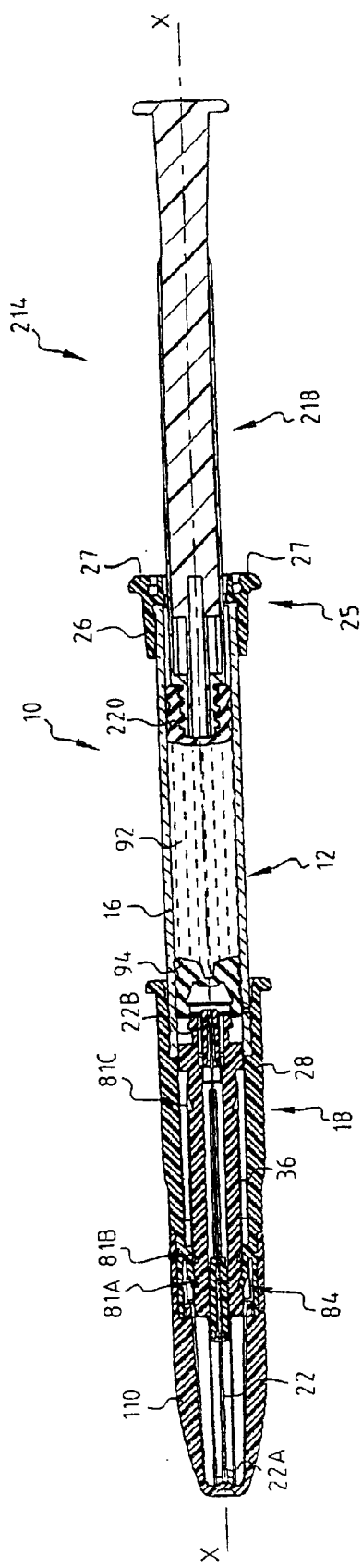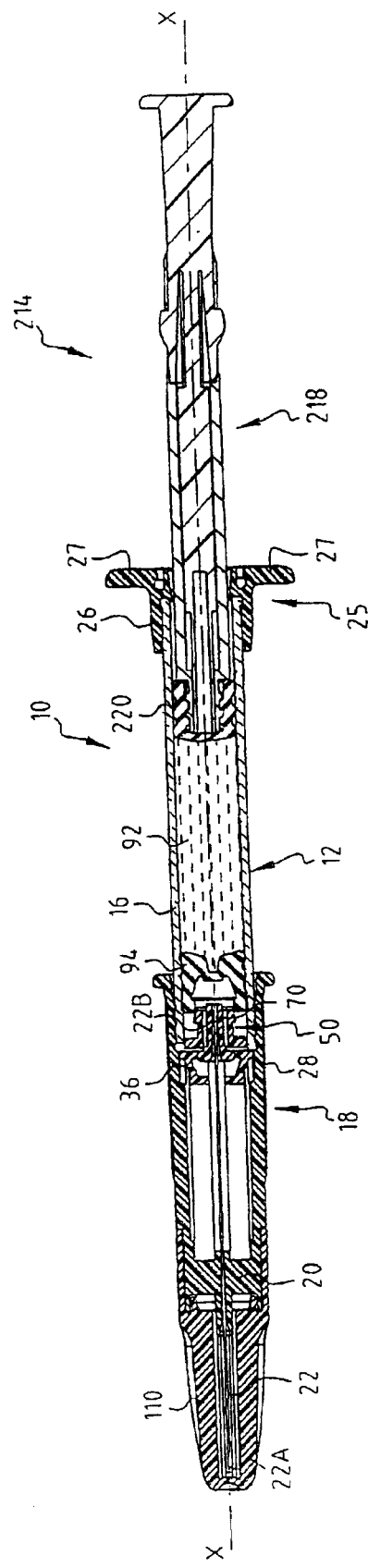
FIG.10A
FIG.10B

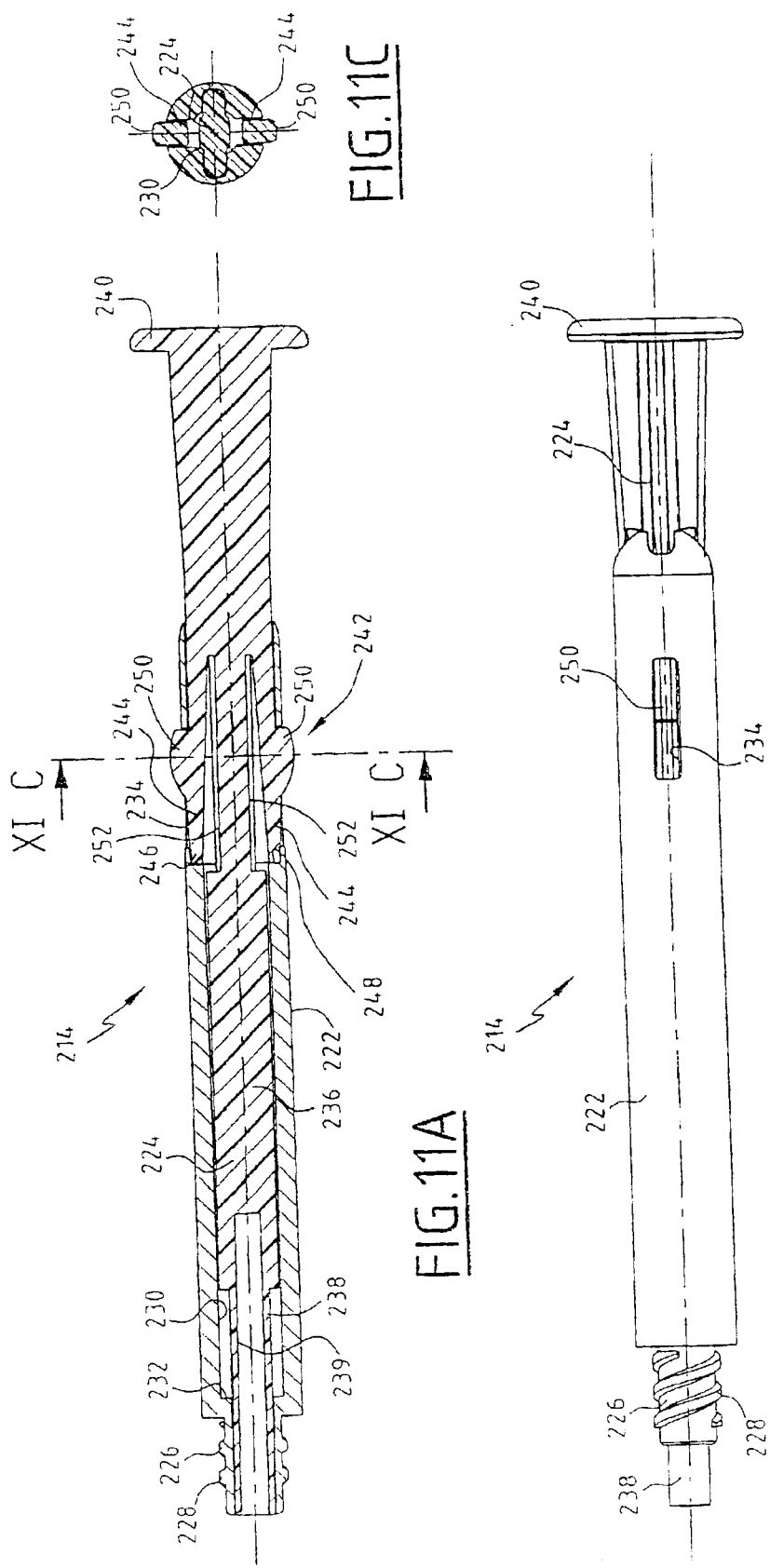

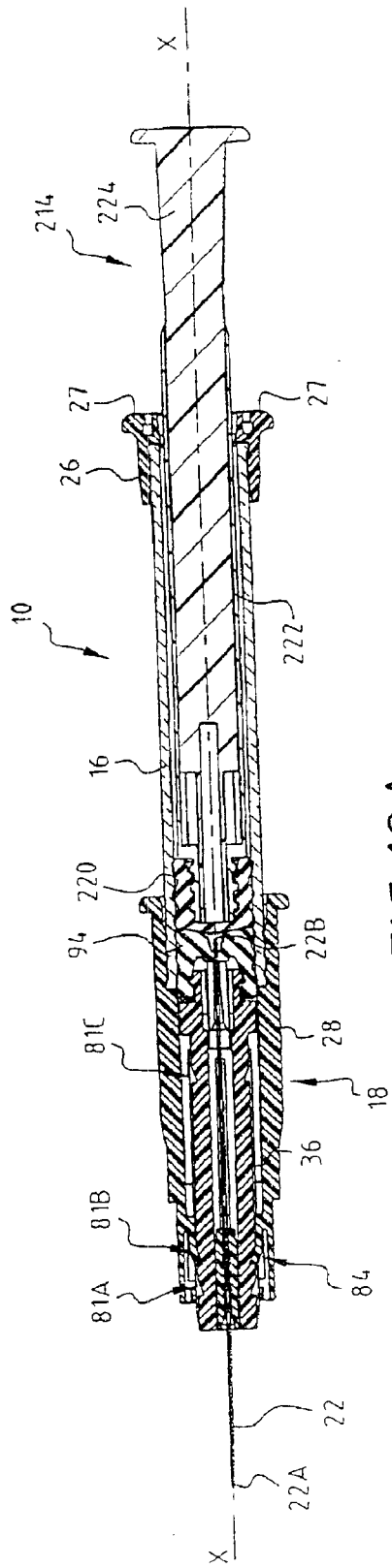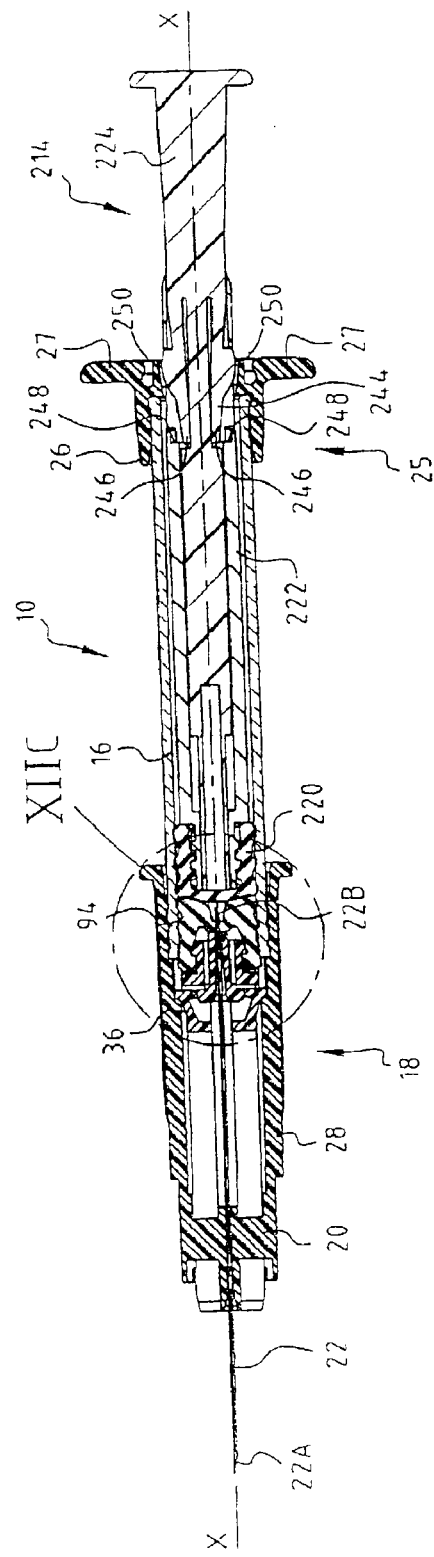

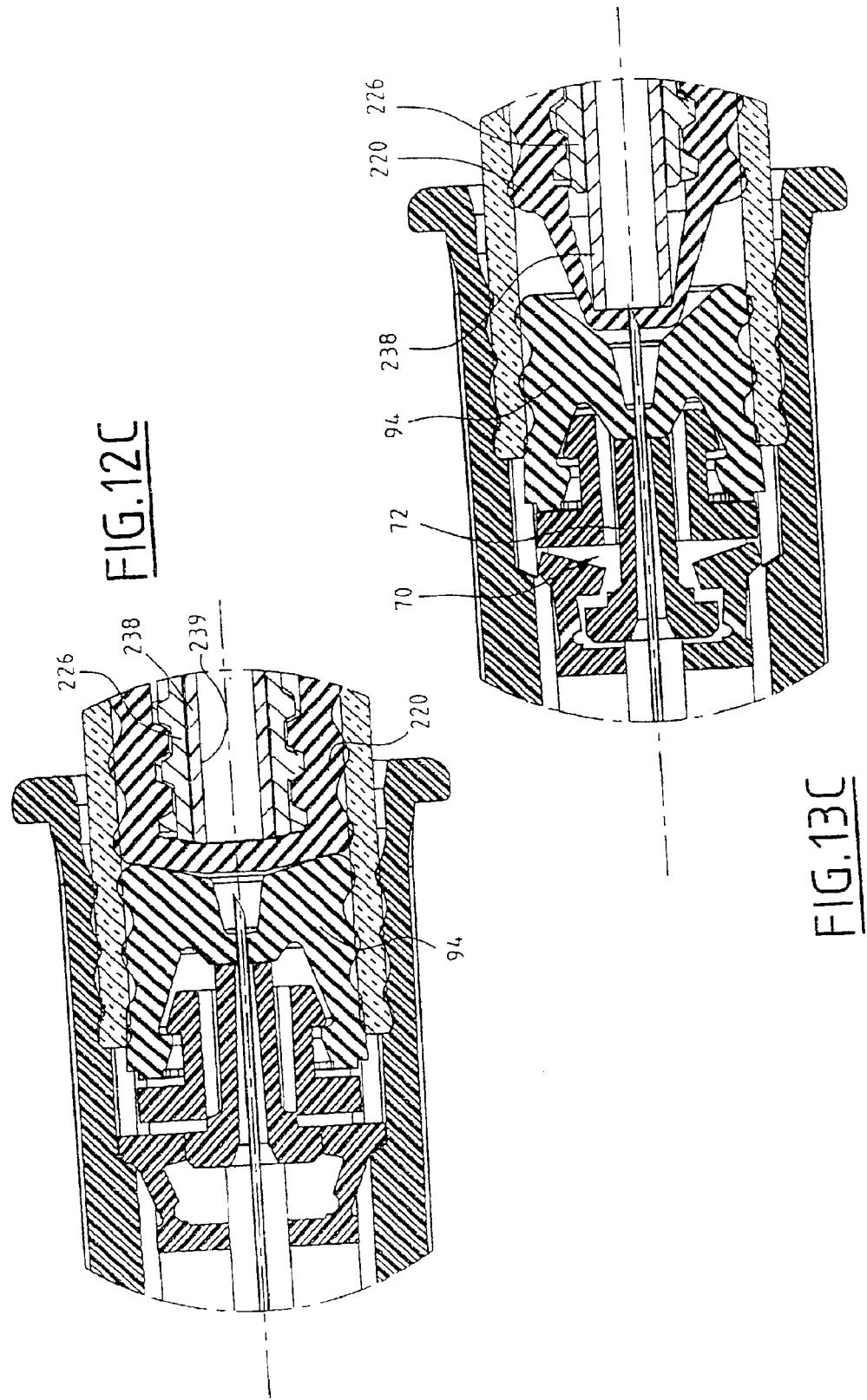

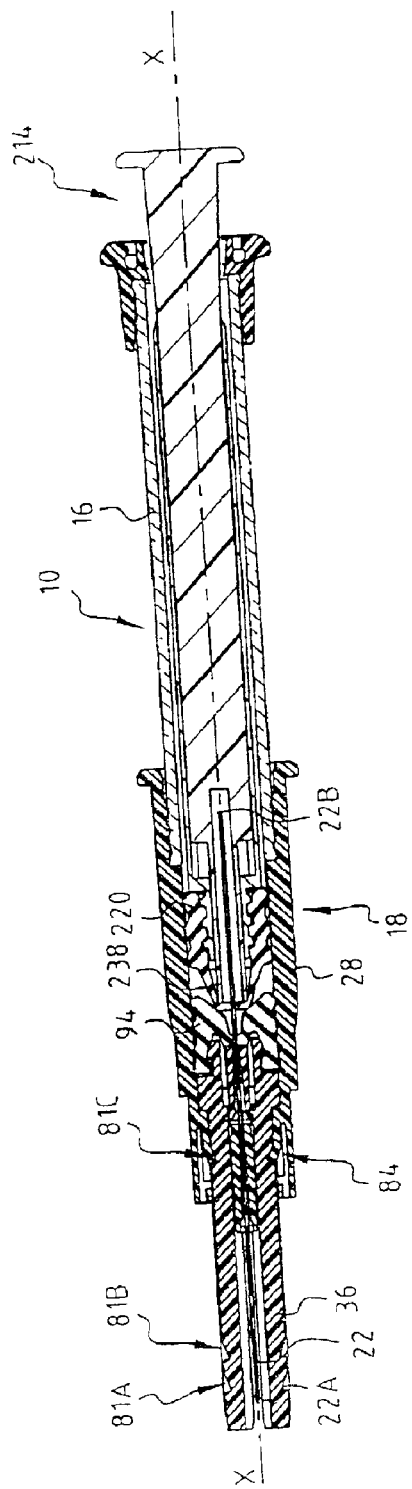
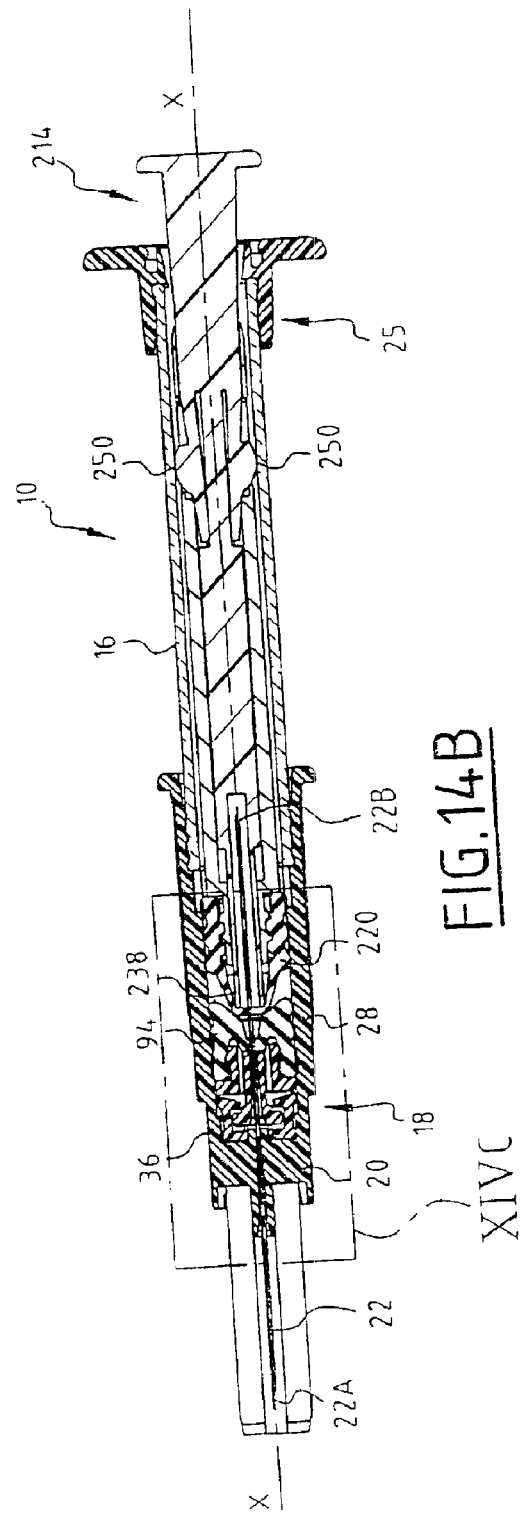

INJECTION SYRINGE WITH MOBILE NEEDLE GUARD

BACKGROUND OF THE INVENTION

The present invention concerns an injection syringe of the type having a syringe body provided with an injection needle and an actuation pusher mounted so as to be able to move in the body, the syringe having a movable guard for protecting the injection end of the needle, which guard is able to move with respect to the body between a position in which it is retracted in the body away from the injection end of the needle and an active protection position in which the front end of the guard is at the front of the injection end of the needle, the guard and the body having associated projecting and recessed reliefs for holding the guard in a retracted position.

A syringe of this type is described for example in the document FR-A-2.757.066.

In this document, the movable guard of the injection end of the needle has legs entering inside the syringe.

The legs have projections adapted to cooperate with the front wall of the body of the syringe in order to keep the guard in its retracted position. The elasticity of the legs of the guard enable the projections to be left free and thus enable the guard to be released.

In practice, it is found that, if a very violent push is exerted on the actuation pusher during injection, the pressure exerted on the needle guard is such that this may be released and move forwards. The intermediate perforatable piston of the syringe being moved forwards, and it is then no longer possible to inject all the content of the syringe.

SUMMARY OF THE INVENTION

The aim of the invention is to afford a solution to this problem by in particular limiting the risks of unintentional movement of the needle guard towards its active protection position during injection.

To this end, the subject matter of the invention is a syringe of the aforementioned type, characterised in that it has a retractable member for the positive retaining of the engagement of the said associated projecting and recessed reliefs, when the guard is in a retracted position, and in that the actuation pusher and the said retaining member are adapted for a retraction of the said retaining member with respect to the needle guard, under the action of the pushing in of the actuation pusher into the body, at the end of injection, providing a release of the positive retaining of the engagement of the associated projecting and recessed reliefs.

According to particular embodiments, the syringe can have one or more of the following characteristics:

- the needle guard and the retractable retaining member are made in one piece;
- the retractable retaining member and the needle guard are initially connected by a breakable link;
- the said associated projecting and recessed reliefs comprise at least one recess provided in the syringe body and at least one elastic arm carrying an external projection adapted to be received in an associated recess in the body, and the said retaining member has at least one stop for holding the external projection or projections in the associated recess, before retraction of the said retaining member;
- the said elastic arms are provided by the rear end portion of the needle guard turned towards the rear actuation piston;
- the said injection needle is extended axially inside the body as far as a rear end of the injection needle, away from which there is initially disposed, in the body, a perforatable transverse wall, the needle and the said transverse wall being able to move with respect to each other from an initial position in which the transverse wall is distant from the needle as far as a final position in which the transverse wall is pierced by the said needle;
- the said retaining member has a passage for the axial guidance of the rear end of the needle, when the transverse wall is perforated;
- the said transverse wall is axially deformable under the action of the actuation pusher acting on the said retaining member;
- the said needle guard and the said transverse wall are initially spaced apart from each other, and they have complementary profiles for axial connection by elastic engagement;
- the needle guard and the transverse wall have axial connection means at least when the needle and the transverse wall are in their final position, and the needle guard and the syringe body have complementary projecting and recessed profiles preventing the movement of the needle guard towards the actuation pusher when the needle and the transverse wall are in their final position;
- the needle guard has at least two legs extending generally parallel, which legs are made in one piece and connected to each other at their rear end turned towards the actuation pusher;
- the needle guard has an attached ring connecting the ends of the legs opposite to their end turned towards the actuation piston;
- the needle guard and the syringe body have complementary projecting and recessed profiles preventing the movement of the needle guard towards the actuation pusher when the needle guard is in its initial retracted position; and
- the syringe body has at least one elastic blade and the needle guard has at least one notch adapted to cooperate with the said elastic blade in order to prevent the movement of the needle guard towards the actuation pusher when the needle guard is in its active protection position.

BRIEF DESCRIPTION OF THE DRAWINGS

The invention will be better understood from a reading of the description which follows, given solely by way of example and made with reference to the drawings, in which:

FIG. 1A is a view in longitudinal section of a syringe according to the invention, before use;

FIG. 1B is a view in longitudinal section of the syringe of FIG. 1A in a cutting plane offset angularly by 90°;

FIGS. 4A, 4B, 4C and 4D are views similar to FIGS. 1A, 1B, 1C and 1D respectively after perforation of the intermediate piston;

FIGS. 5A, 5B, 5C and 5D are views similar to FIGS. 1A, 1B, 1C and 1D respectively, at the end of injection, before release of the needle guard;

FIGS. 8A, 8B, 8C and 8D are views similar to FIGS. 1A, 1B, 1C and 1D respectively, at the end of the fitting of the needle guard in its active protection position;

FIG. 9 is a view in longitudinal section of the front end of another embodiment of a needle guard used in a syringe according to the invention;

FIGS. 10A and 10B are views similar to FIGS. 1A and 1B of a variant embodiment of a syringe according to the invention;

FIGS. 11A and 11B are views respectively in longitudinal section and externally of the actuation pusher of the syringe of FIGS. 10A and 10B, this being shown respectively in its retracted state and in its deployed state;

FIG. 11C is a view in cross-section taken along the line XI—XI of the actuation pusher of FIG. 11A;

FIGS. 12A, 12B and 12C are views similar to FIGS. 5A, 5B and 5C of the variant embodiment of the syringe;

FIGS. 13A, 13B, 13C are views similar to FIGS. 6A, 6B and 6C of the variant embodiment of the syringe; and FIGS. 14A, 14B and 14C are views similar to FIGS. 8A, 8B and 8C of the variant embodiment of the syringe.

DETAILED DESCRIPTION OF THE INVENTION

Figure 1C:
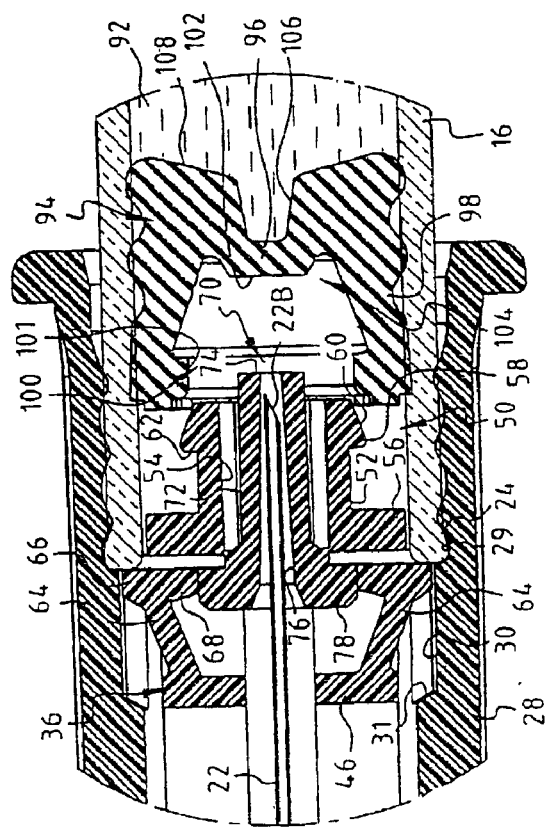
FIG. 1C is a larger-scale view of the rear end of the needle guard in the cutting plane of FIG. 1B.

The injection syringe 10 depicted in FIG. 1, with an overall shape generated by rotation, of axis X—X, is a single-use syringe. It is offered ready for use and already containing medical fluid to be injected. It comprises essentially an elongate syringe body 12 and an actuation pusher 14 mounted so as to be able to move inside the body 12.

The syringe body 12 is formed by a tube 16, at the front end of which a needle support 18 is fixed. This needle support has a crosspiece 20 forming the front wall of the syringe body. This crosspiece 20, visible in FIG. 1B, is provided with an injection needle 22 passing through. The latter has a front injection end 22A projecting with respect to the body 12. The needle is extended axially inside the body 12 as far as a rear end 22B.

The tube 16 is produced for example from glass and has a circular cross-section. Its front end is provided externally with a peripheral rim 24 visible in FIG. 1C. This rim is intended for holding the needle support 18. At the rear end of the tube 16 there is attached a gripping member 25 facilitating the gripping of the syringe body between the index and middle fingers. This comprises a sleeve 26 snapped externally on the end of the tube 16 and two diametrically opposed lugs 27 for supporting the fingers.

Figure 2:
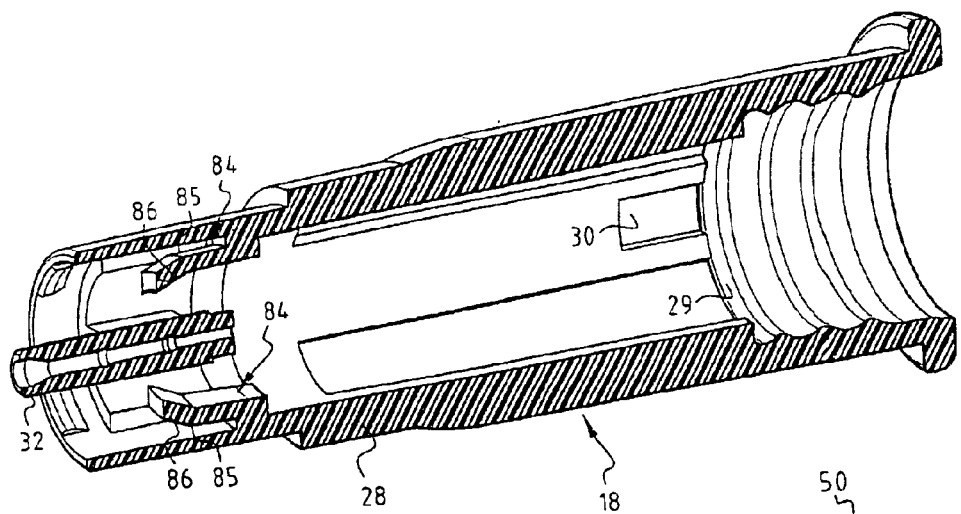
FIG. 2 is a view in perspective and longitudinal section of the needle support of the syringe according to the invention.

The needle support 18 is shown in section in FIG. 2. It is delimited externally by a sleeve 28. The crosspiece 20 is made in one piece with the sleeve 28 in the vicinity of its front end, where it extends along a diameter of the sleeve. On the internal wall of the sleeve 28 there is provided, close to its open end opposite to the crosspiece 20, a peripheral groove 29 for receiving the rim 24.

Immediately in front of the peripheral groove 29, on the same side as the crosspiece 20, two recesses 30 are provided in the internal surface of the sleeve 28. These recesses 30 have, at their end turned towards the crosspiece 20, a ramp 31 providing a progressive reduction in the depth of the recess in the direction of the crosspiece 20, that is to say towards the front end of the syringe.

The crosspiece 20 has an axial stud 32 made in one piece, which holds the injection needle 22. This stud, visible in FIG. 1D, is directed towards the injection end 22A of the needle and is received inside the space delimited by the sleeve 28.

Two identical passages 34, in the shape of a half-moon, are delimited on each side of the partition 20 inside the sleeve 28.

Figure 3A:
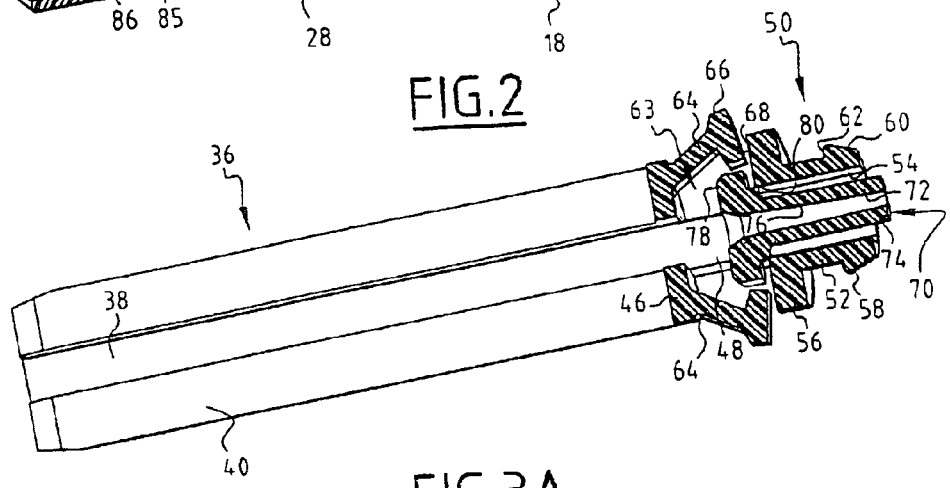
FIG. 3A is a perspective view of the needle guard of the syringe according to the invention before mounting in the syringe.
Figure 3B:
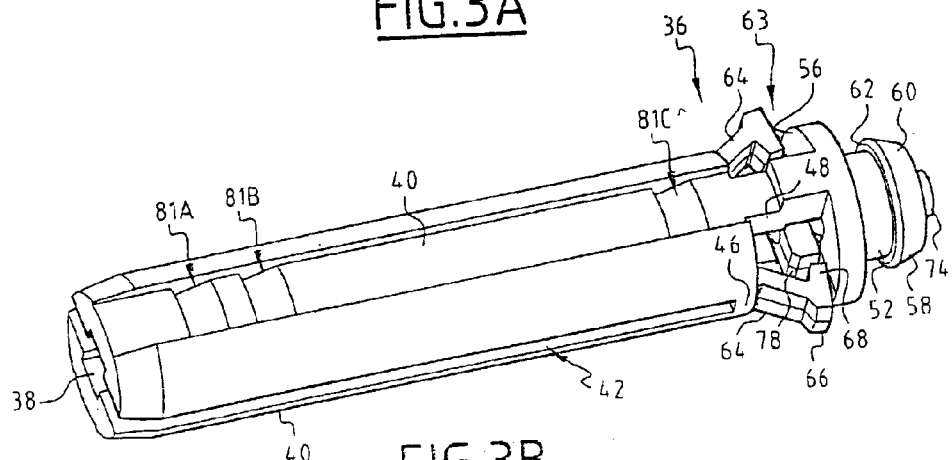
FIG. 3B is a view in perspective and longitudinal section of the needle guard before mounting in the syringe.

These passages 34 provide guidance for a needle guard 36 shown alone in FIGS. 3A and 3B.

The needle guard 36 has a generally elongate shape. It has an axial pipe 38 passing axially right through it. The guard 36 is split longitudinally over the main part of its length from its front end and thus delimits two legs 40 extending parallel to each other on each side of the slit denoted 42. The two legs are connected to each other close to the rear end of the needle guard by an annulus 46 made in one piece. The two legs 40 and the annulus 46 form the body of the guard. Each of the legs is extended by two pillars 48 extending beyond the annulus 46. The pillars 48 are connected opposite the legs 40 by a head 50 generated by rotation and extending along the axis of the needle guard. This head 50 has a generally cylindrical wall 52 delimiting an internal passage 54. At its end turned towards the legs 40, the cylindrical wall 52 has an external collar 56. At its other end, the cylindrical wall 52 is bordered by an external snapping-on rim 58 having a frustoconical surface turned towards the end of the head 50, this frustoconical surface ending in a shoulder 62 facing the collar 56.

In the gap 63 delimited between the annulus 46 connecting the legs and the head 50 there extend two elastic arms 64 connected at one of their ends to the annulus 46, with which they are made in one piece. These arms are generally rectilinear and have a free end. At rest, they extend in a plane passing through the axis of the needle guard and separate progressively from the axis thereof towards their free end.

At its free end, each arm has an external projection 66 turned in the opposite direction to the axis of the guard. This projection is adapted to engage in a recess 30 in the needle support.

In addition, at this same end, each arm 64 has an internal projection 68 turned towards the axis of the guard.

A retractable member 70 for the positive holding of the arms 64 in a separated position is initially disposed partially between the ends of the arms 64. This holding member has a tubular body 72 extending initially inside the pipe 54 along the axis of the guard. The length of the tubular body 72 is such that its free end denoted 74 projects beyond the rear end of the head 70 along the axis of the guard.

Internally, the tubular body 72 defines a generally frustoconical passage 76 for guiding and centring the rear end 22B of the needle.

At its front end, extending initially between the free ends of the arms 64, the holding member 70 has externally two diametrically opposed protrusions 78. These are adapted to form support stops for the internal projections 68 thus holding the arms 64 separated and the external projections 64 in the recesses 30 in the needle support.

At its external periphery, the holding member 70 is connected to the head 50 of the needle guard by a breakable link 80 formed by a web connecting the holding member and the head 50, the head and the holding member being made in one piece with each other through this web at the end of the passage 54.

Figure 1D:
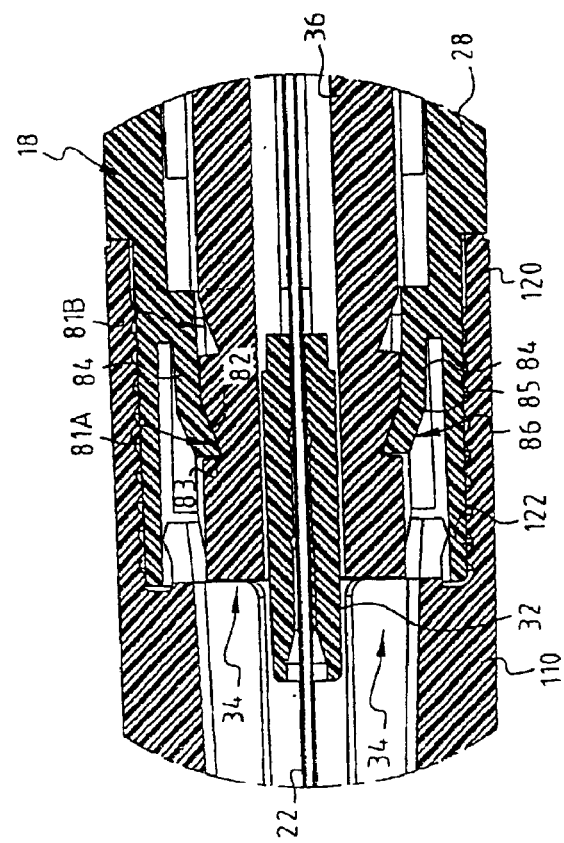
FIG. 1D is a larger-scale view of the front end of the needle guard in the cutting plane of FIG. 1B.

As shown in FIG. 1C, before use of the syringe, the rear end 22B of the needle extends in the passage 76, so that the end of the needle is completely covered by the holding member 70.

Each leg 40 of the guard has, on its lateral surface, three notches 81A, 81B, 81C disposed longitudinally in this order, from the front end of the legs of the guard as far as their rear end where the two legs are connected by the annulus 46.

The notches 81A and 81B are disposed close to each other in the immediate vicinity of the front end of the legs 40. On the other hand, the notch 81C in each leg is disposed immediately in front of the annulus 46.

The three notches have identical profiles. As illustrated for example in FIG. 1D, each notch has an inclined ramp 82 from the lateral surface of the leg towards the bottom of the notch, in a direction going from the rear of the leg towards the front thereof. This ramp 82 is followed, towards the front of each leg, by a shoulder 83 forming a stop.

The notches 81A, 81B and 81C constitute recessed reliefs adapted to cooperate with associated projecting reliefs provided on the needle support 28 in order to prevent rearward return of the needle guard from three positions corresponding to each of the notches.

The complementary projecting profiles carried by the needle guard 28 are formed by elastic blades 84 made in one piece with the sleeve 28 of the needle support. These elastic blades project with respect to the internal lateral surface of the sleeve.

The elastic blades 84 are connected to the sleeve 28 only at their rear end. They extend generally parallel to the axis of the syringe and their free end is turned towards the injection end 22A of the needle. Each elastic blade has an elbow 85 extended by a projecting locking portion 86 turned towards the axis of the syringe. This projecting locking portion 86 is adapted to be received successively in each of the notches 81A, 81B. In particular, the end of the locking portion 86 is adapted to come into abutment against the shoulder 83 of each of these notches and to slide on the ramps 82 in order to cause an elastic deformation of the associated blade.

The actuation pusher 14 has a piston rod 87 with a cruciform cross-section and having, at its rear end, a pad 87A for supporting the thumb of the operator. At its opposite end the piston rod 87 has a generally frustoconical axial protuberance 88 whose diameter decreases towards its free end. The maximum diameter of this protuberance is less than the cross-section of the passage 54 provided in the head of the guard. A housing 89 open on the front is provided axially in the piston rod 87.

This housing serves for receiving the rear end 22B of the needle at the end of injection. The housing 89 has an elongate shape along the axis X—X and a circular cross-section.

The housing 89 is closed off by an end piston 90 in the form of a bowl forming a rear piston of the syringe. This piston 90 has a cylindrical side wall 91A closed off by a disc 91B forming the bottom of the bowl. The side wall 91A is provided on the inside with successive rims. On its external surface, the piston rod 87 has annular grooves in which the successive rims are received, thus providing an axial connection of the rear piston 90 and piston rod 87. The rear piston 90 is elastically deformable, notably in its part consisting of the disc 91B. The rear piston 90 constitutes a transverse wall adapted to slide sealingly inside the tube 16. The disc 91A can be perforated in its central part.

As depicted in FIG. 1A, the fluid to be injected 92 is disposed inside the tube 16 in a space delimited by the rear piston 90 and an intermediate piston 94.

The intermediate piston 94 is shown to a larger scale in FIG. 1C. It is produced from a resilient material such as rubber. It has a transverse wall 96 which can be perforated axially in its central region. This transverse wall is surrounded by a lateral sleeve 98 made in one piece with it. This lateral sleeve is adapted to be pressed sealingly against the internal surface of the tube 19. At its end turned towards the head 50 of the needle guard, the side wall 98 and the transverse wall 96 delimit, in the intermediate piston 94, a chamber 100 having a shape complementary to the external profile of the head 50 delimited by the lateral surface 52 and the snapping-on rim 58. The chamber 100 opens towards the needle guard. It has, at the periphery of its opening, a radially projecting edge 101, adapted to provide the subsequent holding of the head 50 in the chamber.

Thus the chamber 100 is adapted to receive the end of the head 50 and to hold it axially by elastic snapping on.

At the bottom of the chamber 100, the transverse wall 96 has a plane surface 102 turned towards the holding member 70. This surface 102 is adapted to bear along the edge of the body of the holding member 70 from its end 74 projecting with respect to the head 50 of the needle guard.

The surface 102 is formed at the top of a protrusion 104 provided at the bottom of the chamber 100, this protrusion being surrounded by an annular channel. The area of the plane surface 102 is less than the cross-section of the pipe 54 across which the holding member 70 is mounted.

Along its face turned towards the actuating pusher 14, the intermediate piston 94 has, at its centre, a well 106, whose periphery is connected to the side wall 98 by a frustoconical surface 108 splaying progressively in the direction of the actuation pusher 14.

This frustoconical surface 108 constitutes an abutment seat for the end of the actuation pusher 14.

As illustrated in FIG. 1C, the intermediate piston 94 is disposed initially immediately behind the rear end of the needle guard 36. In particular, the head 50 of the guard is outside the chamber 100. In this initial position, the rear end 22B of the needle is away from the perforatable transverse wall 96.

In a variant, the intermediate piston 94 is initially engaged around the head 50 of the guard. The rear end 22B of the needle is however away from the perforatable wall 96, this end being disposed in the passage 76.

In addition, a cap 110 for guarding the needle 22 is engaged around the sleeve 28 of the needle support and covers the injection end 22A of the needle.

As illustrated in FIG. 1D, the cap 110 has, at its open end, a skirt 120 delimiting an annular space inside which the end of the needle support 18 is received.

The external lateral surface of the needle support 18 and the internal lateral surface of the skirt 120 are pressed against each other.

One of these surfaces advantageously has a helical channel 122 opening out, at one end, outside the syringe, when the cap is fitted on the needle support 18, the other end of the channel 122 opening out inside the cap.

This helical channel 122 is produced in the skirt 120 in the embodiment envisaged. It provides the circulation of gases between the outside and inside of the needle guard when this is in place on the needle support. Thus this channel makes it possible to sterilize the syringe equipped with its needle guard in an autoclave or any other sterilization device.

The syringe is assembled in the following manner.

The needle 22 is bonded through the needle support 18. The guard 36 is introduced into the needle support 18 through its rear end, that is to say on the same side as the end 22B of the needle. The guard 36 is mounted through the needle support 18 by engaging the legs 40 in the passages 34 surrounding the stud 32. The legs then extend along the rear part of the needle 22. In this position, the projecting ends 86 of the elastic blades 84 are received in the notches 81A, preventing removal of the guard by traction from its rear end. The front cap 110 is then put in place by fitting it around the sleeve 28.

The needle support 18, thus provided with the cap 110 and the needle guard 36, can be manipulated without any risk of degradation to the ends of the needle, this being protected at both ends. In particular, it can be distributed on production lines in vibrating bowls.

In parallel to the assembly of the needle support, the tube 16 is provided with the gripping member 25. It is filled with the fluid 92 disposed between the intermediate piston 94 and the actuation pusher 14. The needle support 18 is put in place by snapping on the front end of the tube 16, as shown in FIG. 1C.

In order to proceed with the injection, the operator removes the cap 110. In a conventional manner, the operator then exerts a push on the actuation pusher 14 with his thumb whilst bearing under the lugs 27 with the index and middle fingers.

The pressure thus exerted, transmitted by means of the liquid 92 to the intermediate piston 94, causes the latter to move towards the rear end 22B of the needle.

The piston 94 then engages on the head 50 of the needle guard and is held thereon by elastic engagement of the re-entrant edge 101 bordering the opening of the chamber at the rear of the snapping-on rim 58 of the head.

In this position, the flat surface 102 provided at the bottom of the chamber bears on the rear end of the retractable holding member 70, as illustrated in FIG. 4C.

The subsequent movement of the piston 94 associated with the needle guard results in the piston 94 impaling itself on the rear end 22B of the needle. In particular, the wall 96 of the intermediate piston is perforated during its movement.

When the transverse wall 96 is perforated by the rear end 22B of the needle, the conduit 76 passing right through the holding member 70 ensures holding of the needle exactly along the axis of the syringe, thus guaranteeing that the perforation of the wall takes place at its middle and exactly in the direction of the axis of the syringe.

Easy subsequent movement of the piston 94 over the entire internal portion of the needle 22 is thus guaranteed.

The continuation of the pushing in of the actuation pusher 14 causes the forward movement of the needle guard 36 coupled to the intermediate piston 94. This movement takes place until the external projections 66 bear against the ramp 31 formed at the front of each recess 30. In this position, illustrated in FIGS. 4A, 4B and 4C, the movement of the needle guard is interrupted, by the abutment of the external projections 66 against the ramp 31. This is because, because of the presence of the protrusions 78 interposed between the free ends of the arms 64, these cannot deform elastically and move closer together, so that the external projections 66 are trapped in the recesses 30, thus preventing a subsequent axial movement of the needle guard 36.

In this position, and as illustrated in FIG. 4D, the projecting portions 86 of the elastic blades 84 are received in the recesses 81B, preventing rearward movement of the needle guard.

The needle guard is then immobilised axially in both directions. This immobilisation is very reliable since on the one hand the special shape of the blades 84 and of the notches 81B prevents rearward return of the guard and on the other hand the protrusions 78 ensure positive holding of the projections 66 in the recesses 30.

After purging of the syringe, the injection end 22A of the needle is inserted into the tissues of the patient.

After insertion of the needle, it is possible to carry out a "vein test", that is to say suction of a drop of blood through the needle by pulling on the actuation pusher 14. Such a test creates no risk of movement of the intermediate piston 94, this being held by the needle guard 36 which is itself immobilised by the elastic blades 84 engaged in the notches 81B.

After completion of the test, the fluid 92 is then injected through the needle 22 under the action of the thrust of the actuation pusher 14 pressed in as far as the position depicted in FIGS. 5A, 5B, 5C and 5D. In this position, most of the fluid 92 is injected and the rear piston 90 comes into contact with the rear surface of the intermediate piston 94.

Throughout the injection, the needle guard 36 is kept immobile through the engagement of the projecting portions 86 of the elastic blades in the notches 81B and through the holding of the external projections 66 in the recesses 30, this holding being guaranteed by the protrusions 84 on the retractable holding member 70.

The holding of the guard is achieved in a reliable manner whatever the force applied to the pusher 14 because of the positive locking of the guard provided by the holding member 70.

At the end of the injection phase, the rear piston 40 comes into abutment against the intermediate piston 94, which is carried by the needle guard which is immobilised axially by the abutment of the external projections 86 against the ramps 31.

When the pressing in of the actuation pusher 14 is continued, and as illustrated in FIGS. 6A, 6B, 6C and 6D, the frustoconical end 88 of the piston rod causes an elastic deformation of the transverse disc 91B of the rear piston 90. This presses on the seat 108 formed on the intermediate piston 94. Under the action of the thrust exerted by the piston rod 87 through the rear piston 90, the intermediate piston 94 deforms by compressing axially. This deformation thus causes a forward movement of the transverse wall 96 and in particular of the surface 102 in abutment on the end 74 of the retractable holding member 70. Under the action of this thrust, the holding member 70 is detached from the head 50 of the needle guard, the breakable connection 80 being broken under the effect of the thrust force.

Under these conditions, the holding member 70 thus disconnected from the remainder of the needle guard 36 moves axially towards a retracted position in the direction of the front end 22A of the needle. In particular, the protrusions 78 initially forming a wedge between the internal projections 68 are moved in front of these projections, thus freeing the movement of the free ends of the arms 64.

Figure 6A:
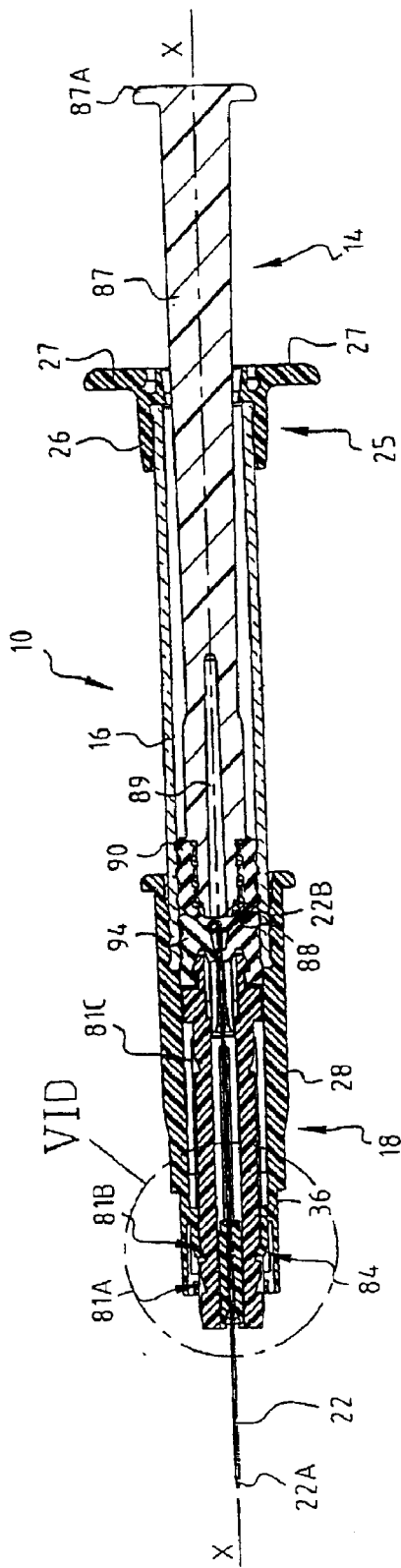
FIGS. 6A, 6B, 6C and 6D are views similar to FIGS. 1A, 1B, 1C and 1D respectively, after release of the needle guard.
Figure 6B:
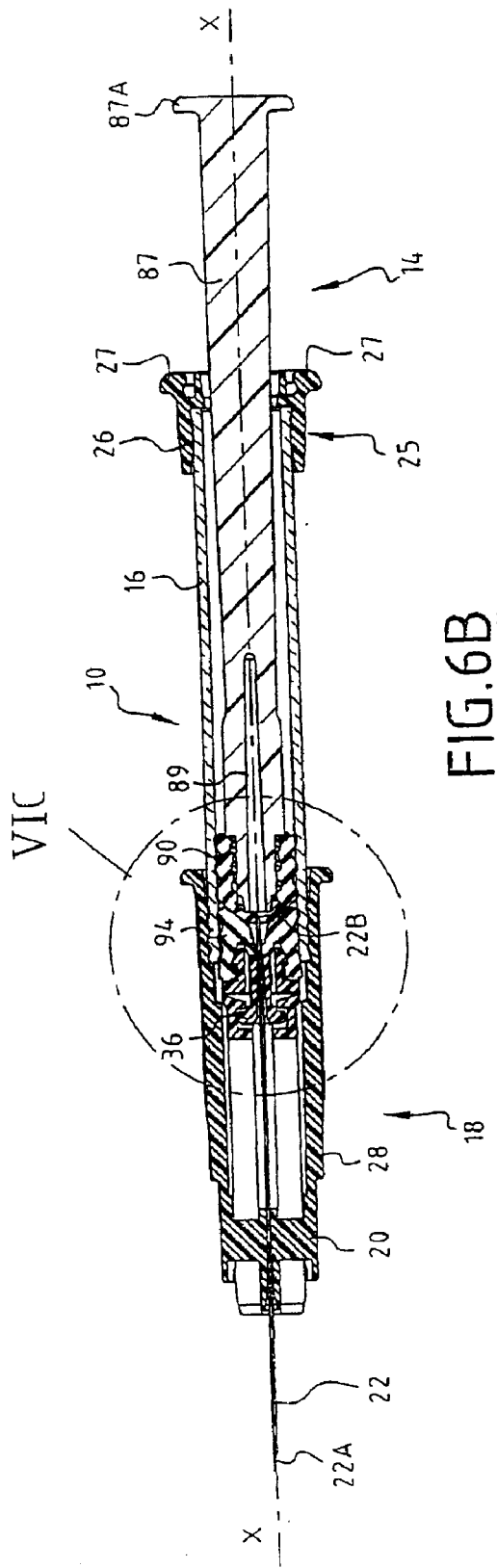
Figure 6C:
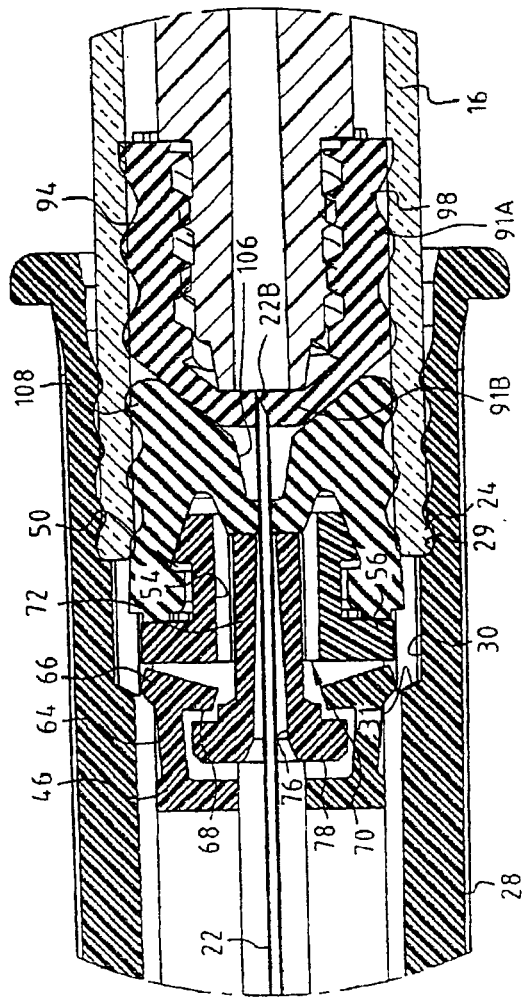
Figure 6D:
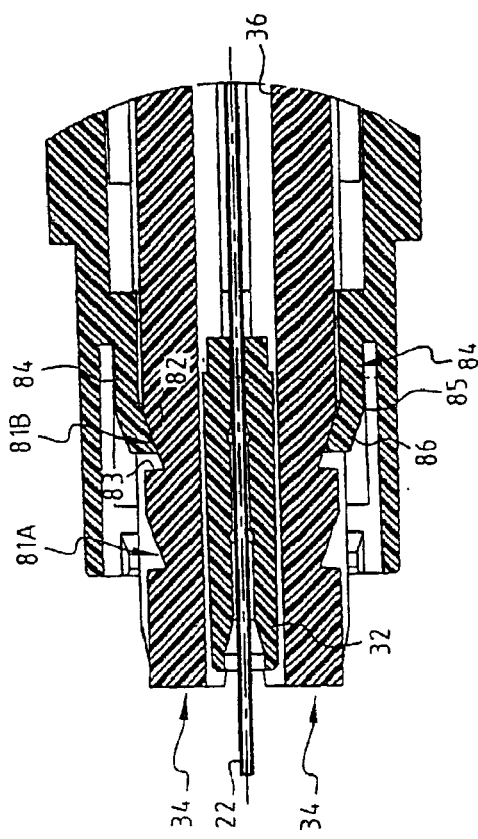
Figure 7A:
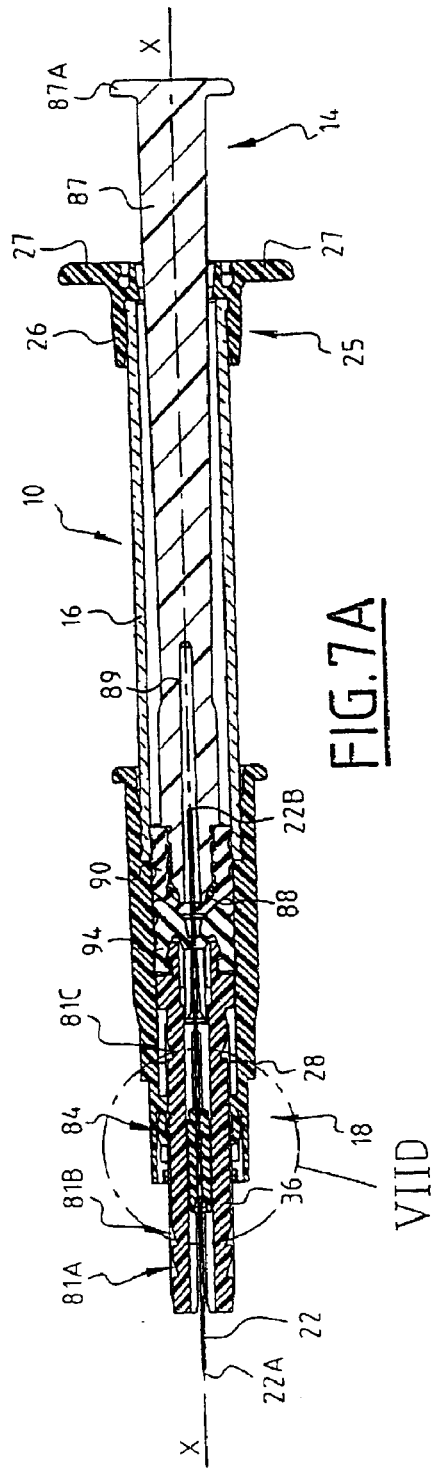
FIGS. 7A, 7B, 7C and 7D are views similar to FIGS. 1A, 1B, 1C and 1D respectively, when the needle guard is put in place.
Figure 7B:
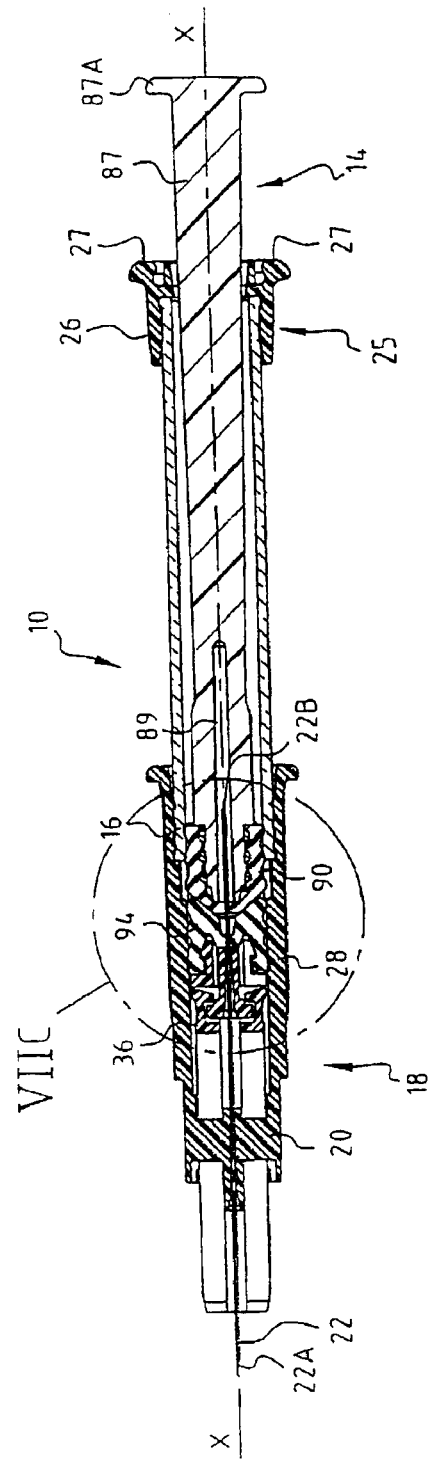
Figure 7C:
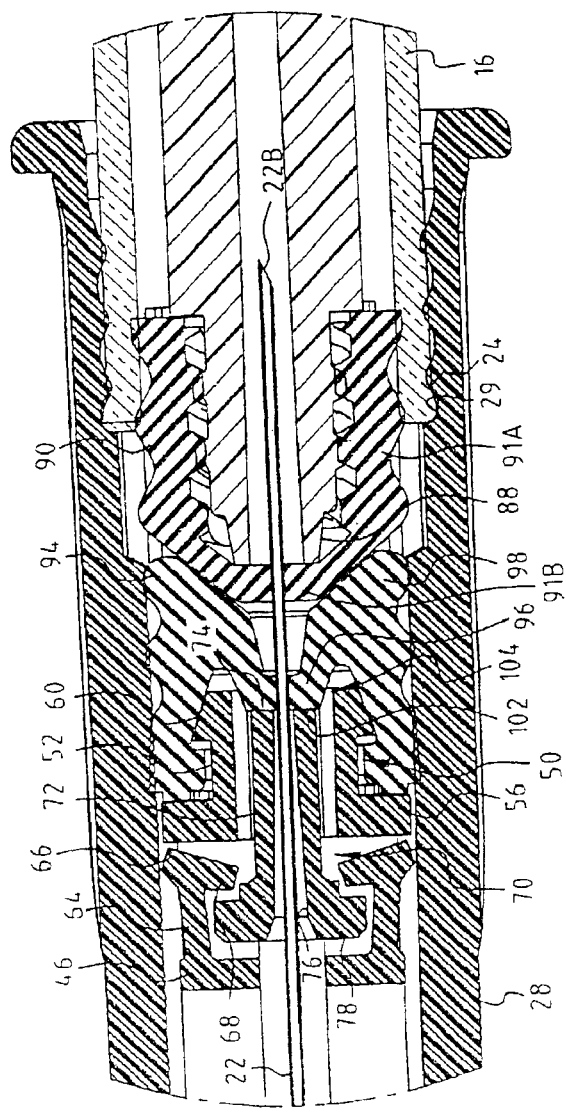
Figure 7D:
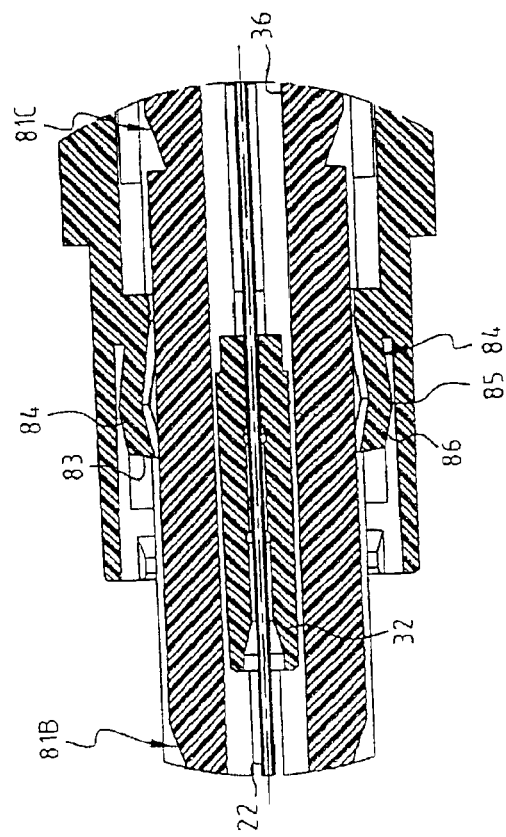

As illustrated in FIG. 6C, when the piston rod 87 moves, the arms 64, freed from the holding member 70, are deformed elastically under the action of the cooperation of the external projections 66 with the ramps 31 which form cam surfaces.

The needle guard 36 is then free to move axially towards the injection end of the needle under the action of the thrust exerted by the actuation pusher 14.

When the pushing in of the pusher 14 is continued, and as illustrated in FIGS. 7A, 7B, 7C and 7D, the legs 40 of the needle guard move progressively along the portion of the needle projecting out of the needle support 18.

When the needle guard 36 moves, the rear end 22B of the needle enters inside the chamber 89 after having perforated the rear piston 90.

Figure 8A:
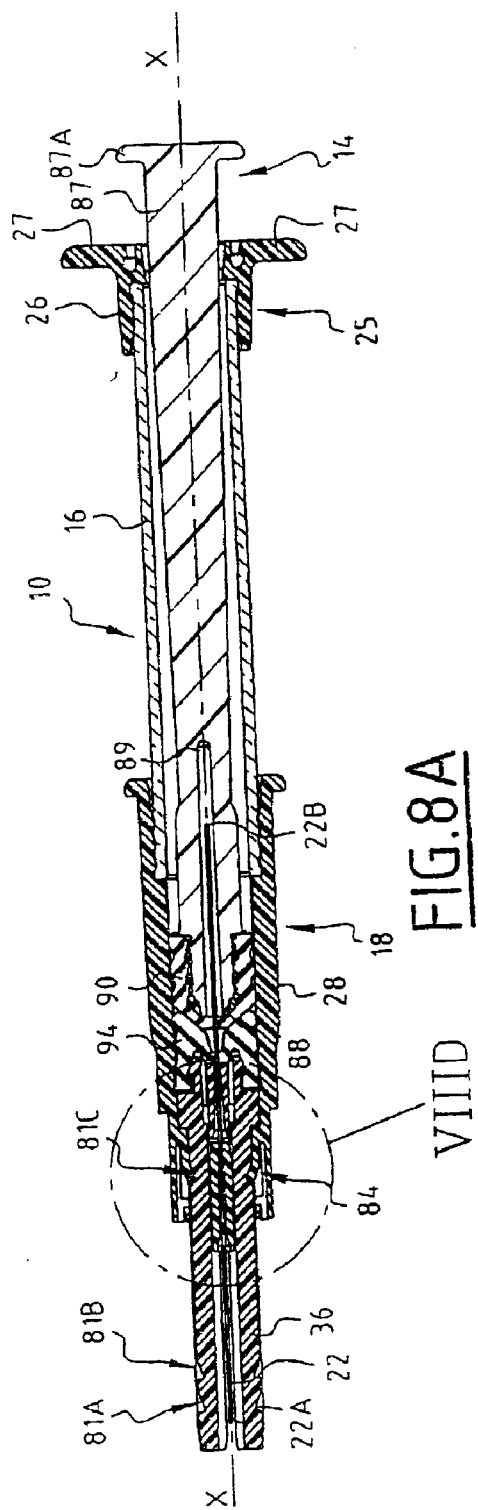
Figure 8B:
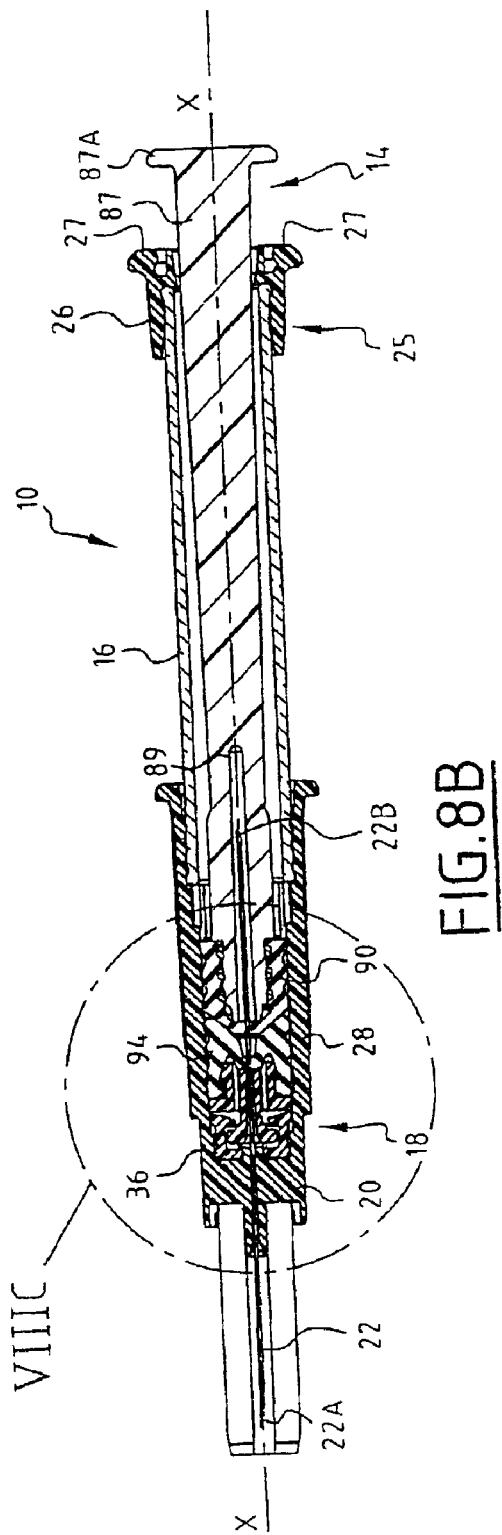

The movement of the needle guard 36 takes place under the action of the pusher 14 until the needle guard comes into contact with the crosspiece 20, as illustrated in FIGS. 8A, 8B and 8C. In this position, and as illustrated in FIG. 8D, the ends of the elastic blades 84 are received between the notches 81C, thus ensuring axial locking of the needle guard, preventing its rearward return.

When the needle guard is in its active guarding position, as illustrated in FIGS. 8A and 8B, the front end of the needle guard extends in front of the front end 22A of the injection needle, preventing any risk of pricking from the end of the needle.

FIG. 9 depicts a variant embodiment of a needle guard used in a syringe as described in the previous figures.

In this embodiment, the free ends of the legs 80 are equipped with a ring 130 attached by snapping on or any other appropriate connection means. This ring provides a securing and connection of the free ends of the legs. It prevents any risk of seeing the legs of the needle guard separated whilst the latter is in its active position of guarding the needle. FIGS. 10 to 13 illustrate another variant embodiment of a syringe according to the invention.

This embodiment differs solely from the previous embodiment in that the actuation pusher 14 is replaced by a telescopic actuation pusher 214.

The telescopic pusher 214 has a piston rod 218 with a front end on which an end piston is mounted, in the form of a bowl 220 similar to the rear piston 90 of the first embodiment.

As illustrated in FIGS. 11A, 11B and 11C, the piston rod 218 has an external tube 222 and an internal rod 224 mounted so as to be able to move slidably inside the tube 222.

The external tube 222 has an outside diameter very slightly less than the inside diameter of the body of the syringe, that is to say than the diameter of the tube 16 and the cross-section of flow through the gripping member 25. At its front end, the tube 222 has a collar 226 axially extending the tube. On the external surface of the collar there is provided a thread 228 for attachment of the end piston 222.

The tube 222 delimits internally a pipe 230 inside which there is slidably mounted the internal rod 224. The pipe 230 opens out at both ends.

The pipe 230 has, in cross-section, generally the shape of a cross, as illustrated in FIG. 11C.

At its front end, the pipe 230 has a shoulder 232 beyond which the collar 226 extends.

In the vicinity of its rear end, the tube 222 has two oblong apertures 234 able to receive radial protrusions on the rod 224.

The internal rod 224 has a body 236 with a cross-section generally in a cross complementary to that of the pipe 230 in order to provide axial guiding and rotational holding of the rod 224 in the pipe 230.

At its front end, the body 236 of the rod is extended by a tubular portion 238 engaged through the collar 226. The length of the tubular portion 238 is greater than the length of the collar 226. Initially, that is to say in the position in FIGS. 11A and 11B, the tubular portion 238 is completely retracted in the collar 226 and the pipe 230.

The tubular portion 238 internally delimits a housing 239 for receiving the rear end of the needle. This housing is extended inside the body 236 of the rod.

At its rear end, the rod 224 has a pad 240 for supporting the thumb of the user.

According to the invention, means 242 for the temporary axial connection of the rod 224 with respect to the tube 222 are provided in the actuation pusher.

More precisely, these temporary connection means comprise two elastic legs 224 made in one piece with the internal rod 224.

These legs are connected from their rear end to the body 236 of the rod. They each have a free end 246 turned towards the front of the actuation pusher. The legs 244 are formed so that, by elasticity, their free ends 246 tend to move away from the axis of the rod 224. These free ends 246 are adapted to come into abutment axially on shoulders 248 defined in the thickness of the tube 222 in front of the apertures 234 in order to provide the axial immobilisation of the internal rod with respect to the tube.

On their external surface, the legs 244 have protuberances 250 engaged through the apertures 234 and projecting with respect to the lateral surface of the tube 222. These protuberances 250 have, in the direction of the axis of the pusher, a height progressively increasing from the front towards the rear, thus forming a convex cam surface moving away progressively from the axis of the pusher from front to rear.

Housings 252 are provided in the body 236 of the internal rod in line with the legs 244 to allow their partial retraction inside the tube 222 when they are close to the axis of the internal rod.

The position of the apertures 234, and the position of the protuberances 250 on the legs 244, are chosen so that, at the end of injection, whilst the actuation pusher is in abutment against the front piston 94, the protuberances 250 come into contact with the rear end of the syringe body, and more particularly with the rear end of the gripping member 25.

In order to carry out an injection with such a syringe, the same steps as those described with regard to FIGS. 1A, 1B and 4A, 4B are first of all implemented. During the injection stage, the two sliding elements of the telescopic pusher are kept connected axially because of the abutment of the free ends 246 of the legs on the shoulders forming stops 248 provided in the external tube 222. Thus the thrust applied to the pad 240 is transmitted to the tube 222, which pushes the rear piston 220.

As illustrated in FIGS. 12A and 12B, whilst the rear piston 220 is in contact with the front piston 94, as illustrated in FIG. 12C, the protuberances 250 provided on the elastic legs 244 of the rod are pushed towards the inside of the tube 222 by cam effect by coming into contact with the abutment finger 27. The legs 224 are thus deformed, so that their free ends 246 are released from the shoulders 248 and are pushed into the housing 252. The free ends 246 are then retracted in line with the body 236 of the rod.

The ends 246 of the legs being separated from the stops 248, the axial movement of the rod 224 with respect to the tube 222 is made possible, the axial connection means 242 being released.

When the pressing on the pad 240 is continued, the thrust is no longer transmitted to the tube 220, which is kept immobile in abutment against the front piston 94. On the other hand, the rod 224 moves axially inside the tube 222. Under the effect of this movement, the tubular portion 238 projects progressively beyond the collar 226.

Figure 13A:
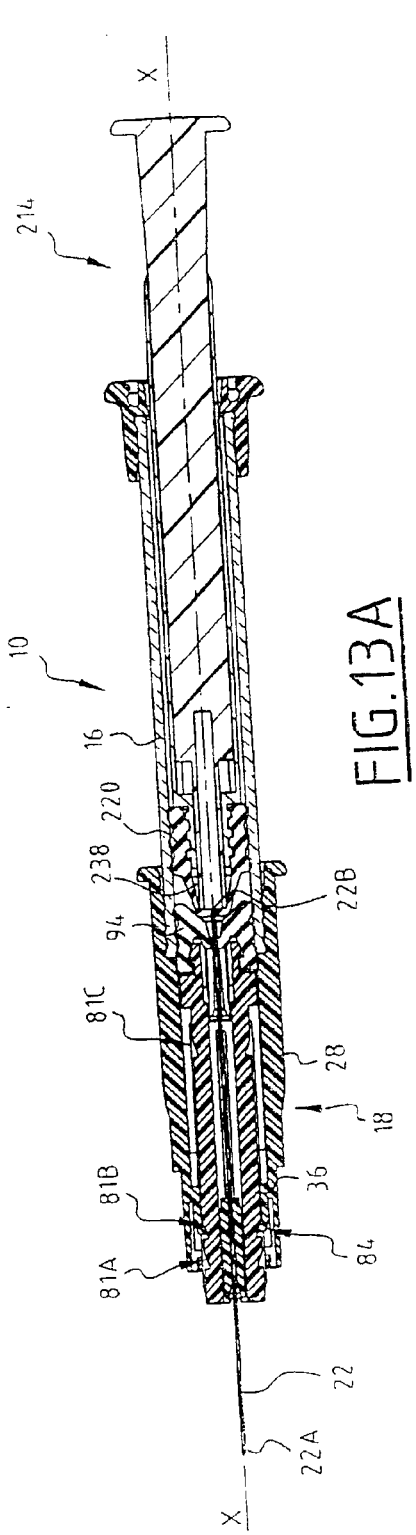
Figure 13B:
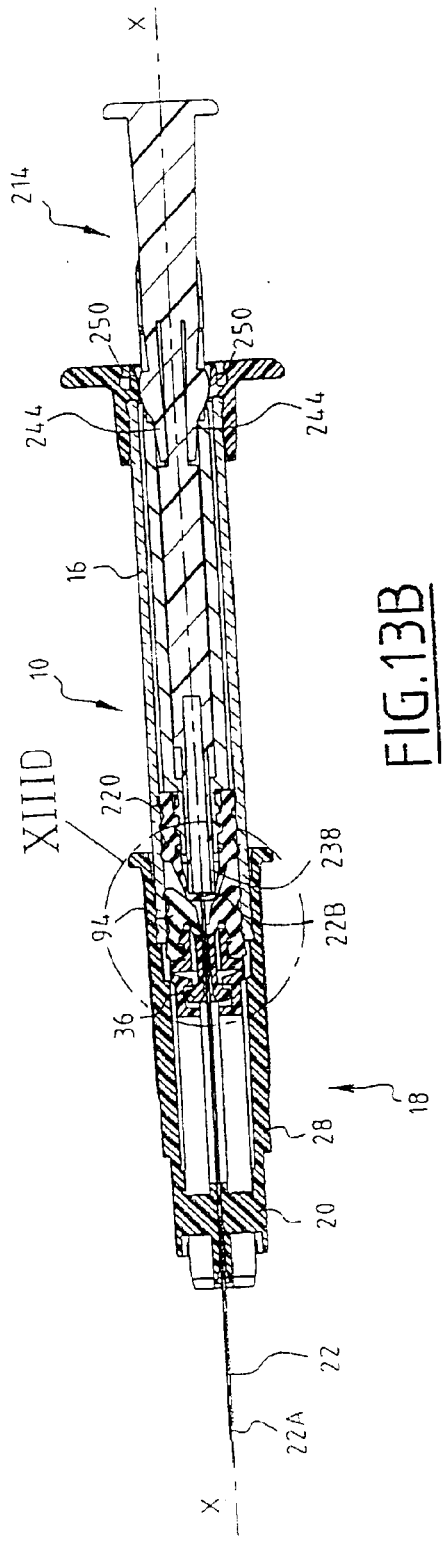

As illustrated in FIGS. 13A, 13B and 13C, the forward movement of the tubular portion 238 causes a deformation of the rear piston 220. The projecting part of the tubular portion 238 acts axially on the holding member 70 by bearing on its rear end 74. As explained with regard to FIG. 6C, the holding member 70 is disconnected from the needle guard and moves axially towards a retracted position. Thus the free ends of the arms 64 are released, so that the needle guard can be moved forwards.

Figure 14C:
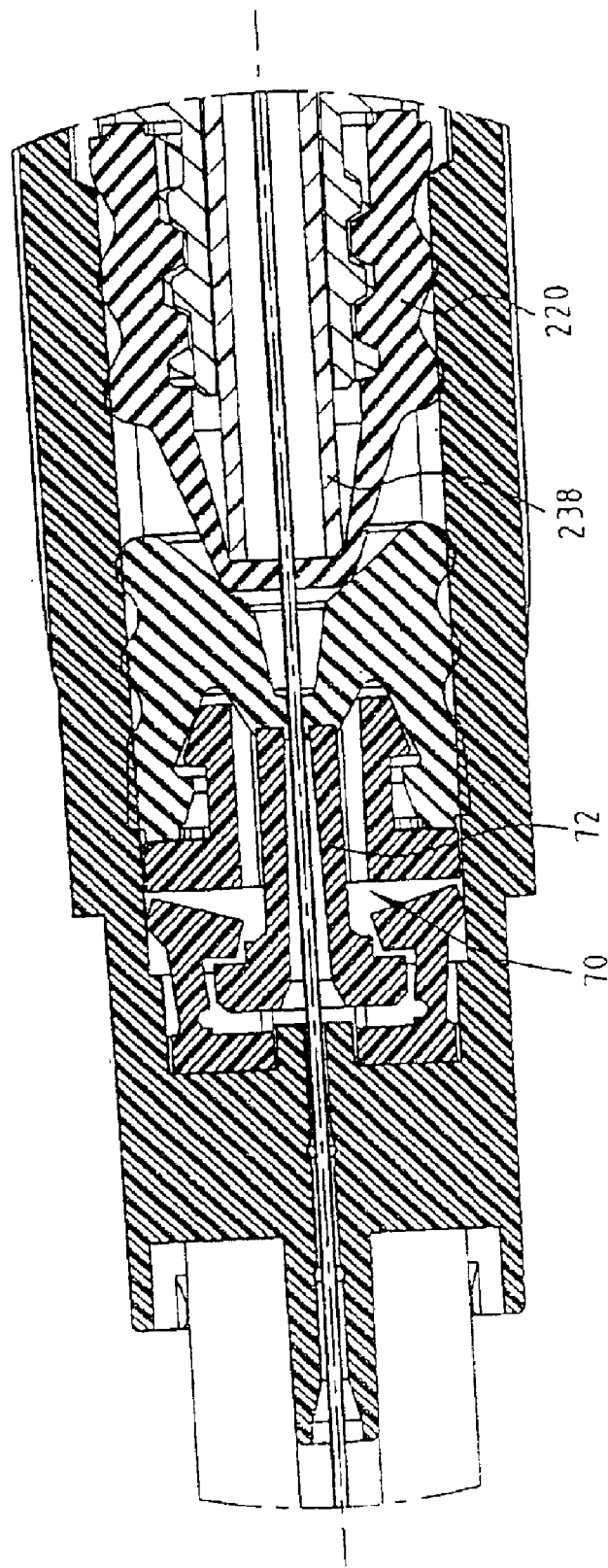

Continuing the pressing on the pad 240 causes the movement of the assembly consisting of the actuation pusher 214 and the needle guard until the front and rear pistons are in the front part of the syringe body, as illustrated in FIGS. 14A, 14B and 14C.

It will be understood that the use of a telescopic pusher, the two movable parts of which are initially axially connected, these two parts being released at the end of the injection phase, avoids having to precisely size the fixed axial protuberance 88 provided at the end of the pusher of the first embodiment. This is because the length of this protuberance must be adjusted precisely in order not to be too long, which may occasion lateral leaks around the piston 90, and not to be too short, which may make it difficult or impossible to move the holding member 70.

In addition, use of the telescopic pusher reduces the force necessary for the movement of the holding member 70. This is because the telescopic pusher 214 acts only the central part of the piston 94 by means of the tubular portion 238 able to move with respect to the tube 222. On the other hand, in the first embodiment, the pusher bears on the entire transverse surface of the piston 94. The force necessary for its deformation is therefore high.

What is claimed is:

1. An injection syringe having a syringe body provided with an injection needle and an actuation pusher mounted so as to be able to move in the body, the injection needle having an injection end and the syringe having a movable needle guard for protecting the injection end of the needle, which guard is able to move with respect to the body between a position in which it is retracted in the body away from the injection end of the needle and an active protection position in which the front end of the guard is at the front of the injection end of the needle, the guard and the body having associated projecting and recessed reliefs for holding the guard in a retracted position, wherein the syringe has a retractable retaining member for the positive retaining of the engagement of the associated projecting and recessed reliefs, when the needle guard is in a retracted position, and wherein the actuation pusher and said retaining member are adapted for a retraction of said retractable retaining member with respect to the needle guard, under the action of the pushing in of the actuation pusher into the body, at the end of injection, providing a release of the positive retaining of the engagement of the associated projecting and recessed reliefs.

2. An injection syringe according to claim 1, wherein the needle guard and the retractable retaining member are made in one piece.

3. An injection syringe according to claim 1, wherein retractable retaining member and the needle guard are initially connected by a breakable link.

4. An injection syringe according to claim 1, wherein said associated projecting and recessed reliefs comprise at least one recess provided in the syringe body and at least one elastic arm carrying an external projection adapted to be received in an associated recess in the body, and said retractable retaining member has at least one stop for holding the or each external projection in the associated recess, before retraction of said retractable retaining member.

5. An injection syringe according to claim 4, wherein said elastic arms are provided by the rear end portion of the needle guard turned towards the rear actuation piston.

6. An injection syringe according to claim 1, wherein said injection needle is extended axially inside the body as far as a rear end of said injection needle, away from which there is initially disposed, in the body, a perforatable transverse wall, the needle and said transverse wall being able to move with respect to each other from an initial position in which the transverse wall is distant from the needle as far as a final position in which the transverse wall is pierced by said needle.

7. An injection syringe according to claim 6, wherein said retractable retaining member has a passage for the axial guidance of the rear end of the needle, when the transverse wall is perforated.

8. An injection syringe according to claim 6, wherein said transverse wall is axially deformable under the action of the actuation pusher acting on said retractable retaining member.

9. An injection syringe according to claim 6, wherein said needle guard and said transverse wall are initially spaced apart from each other, and wherein they have complementary profiles for axial connection by elastic engagement.

10. An injection syringe according to claim 6, wherein the needle guard and the transverse wall have axial connection means at least when the needle and the transverse wall are in their final position, and wherein the needle guard and the syringe body have complementary projecting and recessed profiles preventing the movement of the needle guard towards the actuation pusher when the needle and the transverse wall are in their final position.

11. An injection syringe according to claim 1, wherein the needle guard has at least two legs extending generally parallel, which legs are made in one piece and connected to each other at their rear end turned towards the actuation pusher.

12. An injection syringe according to claim 11, wherein the needle guard has an attached ring connecting the ends of the legs opposite to their end turned towards the actuation piston.

13. An injection syringe according to claim 1, wherein the needle guard and the syringe body have complementary projecting and recessed profiles preventing the movement of the needle guard towards the actuation pusher when the needle guard is in its initial retracted position.

14. An injection syringe according to claim 1, wherein the syringe body has at least one elastic blade and the needle guard has at least one notch adapted to co-operate with the said elastic blade in order to prevent the movement of the needle guard towards the actuation pusher when the needle guard is in its active protection position.

15. An injection syringe according to claim 1, wherein the needle guard is able to move with respect to the syringe body under the action of the progressive pushing in of the actuation pusher in the syringe body.

16. An injection syringe according to claim 1, wherein the actuation pusher comprises two telescopic elements mounted so as to be able to move axially with respect to each other and releasable means for the axial connection of the two elements with respect to each other during the injection phase, and wherein the syringe has means of releasing the means of axial connection of the two elements at the end of injection.

17. An injection syringe according to claim 16, wherein the actuation pusher has an external tube and an internal rod able to slide inside the external tube, which internal rod has a rear end projecting out of the external tube and having an abutment surface for a finger for pressing in the actuation pusher into the syringe body, and wherein the internal rod has an extension able to move, after release of the axial connection means, between an injection position, in which the extension is at least partially retracted in the external tube, and an active position of retraction of the holding member, in which said active position the extension projects with respect to the external tube.

18. An injection syringe according to claim 17, wherein the releasable axial connection means have at least one aperture provided in the external tube and at least one projecting member connected to the internal rod, said at least one projecting member being elastically engaged in the aperture, the aperture having, at one end, a stop for the axial immobilization of the external tube for the abutment of the projecting member engaged in the aperture.

19. An injection syringe according to claim 16, wherein the means of releasing the means of axial connection of the two elements at the end of injection have at least one release member able to co-operate with the syringe body at the end of injection in order to cause the release of the axial connection means.

* * * * *